US009523697B2

(12) United States Patent
Cashman et al.

(10) Patent No.: US 9,523,697 B2
(45) Date of Patent: Dec. 20, 2016

(54) DETECTION OF PATHOGENIC ABETA USING AN EPITOPE PROTECTION ASSAY

(75) Inventors: Neil Cashman, Vancouver (CA); Marty Lehto, Burlington (CA)

(73) Assignee: PROMIS NEUROSCIENCES Inc., Toronto (CA)

( * ) Notice: Subject to any disclaimer, the term of this patent is extended or adjusted under 35 U.S.C. 154(b) by 298 days.

(21) Appl. No.: 12/910,600

(22) Filed: Oct. 22, 2010

(65) Prior Publication Data

US 2011/0124018 A1 May 26, 2011

Related U.S. Application Data

(63) Continuation of application No. 10/568,729, filed as application No. PCT/CA2004/001503 on Aug. 20, 2004, now abandoned.

(60) Provisional application No. 60/496,381, filed on Aug. 20, 2003, provisional application No. 60/497,362, filed on Aug. 21, 2003.

(30) Foreign Application Priority Data

Aug. 20, 2003 (CA) .................................... 2437675
Aug. 21, 2003 (CA) .................................... 2437999

(51) Int. Cl.

| | |
|---|---|
| ***A61K 49/00*** | (2006.01) |
| ***A61K 49/16*** | (2006.01) |
| ***A61K 39/395*** | (2006.01) |
| ***A61K 39/00*** | (2006.01) |
| ***G01N 33/53*** | (2006.01) |
| ***G01N 33/567*** | (2006.01) |
| ***A61B 5/00*** | (2006.01) |
| ***G01N 33/68*** | (2006.01) |
| ***C07K 16/18*** | (2006.01) |
| ***C07K 16/40*** | (2006.01) |
| ***G01N 33/58*** | (2006.01) |
| *A61K 38/00* | (2006.01) |

(52) U.S. Cl.

CPC ........... *G01N 33/6896* (2013.01); *C07K 16/18* (2013.01); *C07K 16/40* (2013.01); *G01N 33/581* (2013.01); *G01N 33/68* (2013.01); *G01N 33/6845* (2013.01); *A61K 38/00* (2013.01); *G01N 2333/90283* (2013.01); *G01N 2800/2828* (2013.01)

(58) Field of Classification Search

CPC ..... C07K 16/18; C07K 16/40; C07K 14/4711; C07K 2317/24; C07K 2317/92; C07K 2317/34; C07K 2317/56; C07K 2317/76; G01N 33/6896; G01N 2333/90283; G01N 2800/2828; G01N 33/68; G01N 33/6845; G01N 2800/2821; G01N 33/53; G01N 2500/00; A61K 38/00; A61K 2039/505; A61K 49/0004

See application file for complete search history.

(56) References Cited

U.S. PATENT DOCUMENTS

| | | | | |
|---|---|---|---|---|
| 4,806,627 | A | 2/1989 | Wisniewski et al. | |
| 4,910,133 | A | 3/1990 | Uda et al. | |
| 4,940,659 | A | 7/1990 | Warrington et al. | |
| 5,834,457 | A | 11/1998 | Bredesen et al. | |
| 5,849,290 | A | 12/1998 | Brown et al. | |
| 6,270,954 | B1 | 8/2001 | Welch et al. | |
| 6,406,864 | B2 | 6/2002 | Prusiner et al. | |
| 6,541,195 | B2 | 4/2003 | Welch et al. | |
| 6,677,125 | B2 | 1/2004 | Prusiner et al. | |
| 6,743,771 | B2 | 6/2004 | Douglas et al. | |
| 6,765,088 | B1 * | 7/2004 | Korth et al. | 530/388.1 |
| 7,041,807 | B1 | 5/2006 | Cashman et al. | |
| 7,439,324 | B2 | 10/2008 | Cashman | |
| 7,510,430 | B2 | 3/2009 | Zhang et al. | |
| 7,625,560 | B2 * | 12/2009 | Basi et al. | 424/145.1 |
| 7,763,710 | B2 | 7/2010 | Cashman | |
| 7,794,692 | B2 | 9/2010 | Chakrabartty et al. | |
| 8,075,891 | B2 | 10/2011 | Cashman | |
| 2002/0123072 | A1 | 9/2002 | Prusiner et al. | |
| 2002/0168684 | A1 * | 11/2002 | Comb et al. | 435/7.1 |
| 2003/0022243 | A1 | 1/2003 | Kondejewski et al. | |
| 2006/0194821 | A1 | 8/2006 | Lansbury et al. | |
| 2006/0211079 | A1 | 9/2006 | Hazen et al. | |
| 2006/0246517 | A1 | 11/2006 | Cashman | |
| 2006/0280733 | A1 | 12/2006 | Kayed et al. | |
| 2007/0003977 | A1 | 1/2007 | Cashman et al. | |

(Continued)

FOREIGN PATENT DOCUMENTS

| | | |
|---|---|---|
| AU | 2004266324 | 8/2004 |
| CA | 2408762 A1 | 4/2003 |

(Continued)

OTHER PUBLICATIONS

Pirttila et al. J. Neurol Sci. Dec. 1, 1994; 127:90-5.*
Otvos et al. Curr. Protein Pept. Sci. Dec. 2002; 3: 643-52.*
Lehto et al. Society for Neuroscience Annual Meeting; Aug. 21, 2002, Program No. 692.9, Abstract.*
Gow et al. FEBS Lett. 1996; 385: 63-66.*
Koppal et al. J. Neurochem. 1999; 72: 310-317.*
Deng H.X. et al., Conversion to amyotrophic lateral, sclerosis phenotype is associated with intermolecular linked insoluble aggregates of SOD1 in mitochondria. Proc. Natl. Acad. Sci., May 2, 2006, pp. 7142-7147, vol. 103, No. 18 National Academy of Sciences, D.C., U.S.A.

(Continued)

*Primary Examiner* — Chang-Yu Wang
(74) *Attorney, Agent, or Firm* — Carmela De Luca; Bereskin & Parr LLP

(57) ABSTRACT

The invention relates to an epitope protection assay for use in diagnosis, prognosis and therapeutic intervention in diseases, for example, involving polypeptide aggregation, such as prion infections. The methods of the invention first block accessible polypeptide target epitope with a blocking agent. After denaturation of the polypeptide, a detecting agent is used to detect protein with target epitope that was inaccessible during contact with the blocking agent.

9 Claims, 9 Drawing Sheets

(56) References Cited

U.S. PATENT DOCUMENTS

| | | | | |
|---|---|---|---|---|
| 2007/0292410 | A1 | 12/2007 | Cashman et al. | |
| 2008/0132685 | A1 | 6/2008 | Chakrabartty et al. | |
| 2008/0206251 | A1 | 8/2008 | Cashman et al. | |
| 2009/0098151 | A1 | 4/2009 | Cashman | |
| 2010/0233176 | A1* | 9/2010 | Cashman et al. | 424/139.1 |
| 2012/0107321 | A1* | 5/2012 | Cashman | 424/139.1 |

FOREIGN PATENT DOCUMENTS

| | | | |
|---|---|---|---|
| CA | 2437675 | | 8/2003 |
| CA | 2437999 | | 8/2003 |
| CA | 2452946 | A1 | 6/2004 |
| CA | 2536305 | | 8/2004 |
| CA | 2437675 | | 2/2005 |
| CA | 2437999 | | 2/2005 |
| CA | 2536305 | | 3/2005 |
| CA | 2642848 | | 3/2007 |
| EP | 0279705 | A2 | 8/1988 |
| EP | 0327337 | A2 | 8/1989 |
| EP | 1668369 | | 8/2004 |
| EP | 04761667.7 | | 8/2004 |
| EP | 4761667.7 | A1 | 6/2006 |
| EP | 7710682.1 | | 5/2007 |
| JP | 63298060 | A | 12/1988 |
| JP | 2003-521477 | | 12/2000 |
| JP | 2006-523496 | | 8/2004 |
| JP | 2010-153006 | | 8/2004 |
| WO | 00/12718 | | 3/2000 |
| WO | WO00/22438 | A1 | 4/2000 |
| WO | WO00/78344 | A1 | 12/2000 |
| WO | WO01/06989 | A2 | 2/2001 |
| WO | 01/96870 | | 12/2001 |
| WO | 2004/024090 | | 3/2004 |
| WO | PCT/CA/2004/001503 | | 8/2004 |
| WO | 2005/019828 | | 3/2005 |
| WO | 2005/077040 | | 8/2005 |
| WO | 2007/025385 | | 3/2007 |
| WO | 2007/067900 | | 6/2007 |
| WO | 2007/098607 | A1 | 9/2007 |
| WO | WO 2010/004209 | A1 | 4/2010 |

OTHER PUBLICATIONS

Furukaway Y. et al., Disulfide cross-linked protein represents a significant fraction of ALS-associated Cu, Zn-superoxide dismutase aggregates in spinal cords of model mice. Proc. Natl. Acad. Sci., May 2, 2006, pp. 7148-7153, vol. 103, No. 18 National Academey of Sciences, D.C., U.S.A.

Kalnine et al., UnitProt Accession No. Q6NR8, Superoxide dismutase 1. [online] May 10, 2005.

Gelinas D.S. et al., Immunotherapy for Alzeheimer's disease, Proceedings for the National Academy of Sciences of the United States of America. Oct. 5, 2004. vol. 101, suppl. 2, pp. 14657-14662.

Griffin and Cashman, Progress in prion vaccines and immunotherapies. Expert Opinion on Biological Therapies. Jan. 6, 2005. vol. 5, No. 1, pp. 97-100.

Valentine J.S. et al, Copper-Zinc Superoxide disumtase and amytrophic lateral sclerosis, Annual Rev. Biochem. 2005; 74: 563-593.

Goodall E.F. et al., Amyotrophic lateral sclerosis (motor neuron disease) proposed mechanism and pathways to treatement, Expert Reviewa in Molecular Reviews, 2006, 8(11): 1-24.

Julien, Mouse models of amyotrophic lateral sclerosis, Elsevier Disease Models, 2006, 3(4): 331-339.

Le Pecheur et al., Oxidized SOD1 alters proteasome activities in vitro and in the cortex of SOD1 overexpressing mice. FEBS Letters, 579(17): 3613-3618, 2005.

Liu H.S. et al, P139 Abstract, An immunization strategy for treating amyotrophic lateral slcerosis that targets misfolded SOD1, Amyotrophic Lateral Sclerosis 2007 (Suppl 1); 8: 140-155, p. 150.

Kerman A, et al., P163 Investigation of Cu/Zn superoxide disumtase misfolding and aggregation in ALS using conformation-specific antibodies. Amyotrophic Lateral Sclerosis 2007 (Suppl 1); 8: 156-177, Abstract p. 164.

Rakhit R, et al. An Immunological epitope selective for pathological monomer-misfolded SOD1 in ALS, Nature Medicine Jun. 2007, vol. 13, No. 6, pp. 754-759.

Kerman A., Amyotrophic lateral slcerosis is a non-amyloid disease in which extensive misfolding of SOD1 is unique to the familial form. Acta Neuropathol, Jan. 2010. 119: 335-344.

Jacobsson et al. Superoxide dismutase in CSF from amyotrophic lateral sclerosis patients with and without CuZn-superoxide dismutase mutations. Brain, 124: 1461-1466, 2001.

Liu et al., Lack of Evidence of Monomer/Misfolded Superoxide Dismutase-1 in Sporadic Amyotrophic Lateral Sclerosis, Ann Neural., 66(1): 75-80, Jul. 2009.

Ezzi, S.A. et al., Wild-type superoxide disumtase acquires binding and toxic properties of ALS linked mutant forms through oxidation, J Neurochem, Jul. 2007; 102(1): 170-8 Epub Mar. 29, 2007.

Bretteschneider, J. et al., Axonal damage markers in cerebrospinal fluid are increased in ALS, Neurology, Mar. 28, 2006, 66(6): 852-6.

Watanabe et al., Adherent Monomer-Misfolded SOD1, PLos ONE, 3(10): e3497, Oct. 2008.

Choi, et al.; Oxidative modifications nd Aggregation of Cu,Zn-superoxide dismutase associated with Alzheimer and Parkinson diseases. The Jourlan of Biological Chemistry, Mar. 25, 2005. pp. 11648-11655, vol. 280, No. 12.

Kayed, R. et al.; Common Structure of Soluble Amyloid Oligomers Implies Common Mechanism of Pathogenesis; Science, Apr. 18, 2003, p. 486-489, vol. 300; AAAS, New York, USA.

Rakhit, R. et al.: Monomeric Cu Zn-superoxide Dismutase Is a Common Misfolding Intermediate in the Oxidation Models of Sporadic and Familial ALS; JBC, Apr. 9, 2004, p. 15499-15504, vol. 279, No. 15; ASBMB, Bethesda, USA.

Kim et al., Non-Specific Binding of Aggregated SOD1 to Antibodies, Abstract for Poster Presentation presented at the 15th International Symposium on ALS/MND, Dec. 2-4, 2004, Philadelphia, U.S.A. and published in ALS and other Motor Neuron Disorders 2004 (suppl 2) pp. 83-84 (Abstract p. 41).

Chakrabartty, Avijit; Oxidation-induced misfolding monomerization and aggregation of SOD1 and its role in ALS, Slides and abstract, presented at the 15th International Symposium on ALS/MND, Dec. 2-4, 2004, Philadelphia U.S.A. and abstract published in ALS and other Motro Nueron Disorders 2004 (suppl 2) 48-49 (Abstract c72).

Deng, et al.: Amyotrophic lateral sclerosis and structural defects in Cu,Zn superoxide disumtase; Science, Aug. 20, 1993. pp. 1047-1051, vol. 261. AAAS, New York, U.S.A.

Rakhit R, et, al. ; Oxidation-induced misfolding and aggregations of superoxide dismutase and its implications for amyotrophic lateral sclerosis. J Biol Chem. Dec. 6, 2002, pp. 47551-47556, vol. 277, No. 49. ASBMB, Bethesda, U.S.A.

Khare, et al.: Sequence and structural determinants of Cu, Zn superoxide dismustae aggregation. Proteins. Nov. 15, 2005; pp. 617-632, vol. 61, No. 3, Wiley-Liss, New York, U.S.A.

Elam J.S., et al.: Amyloid-like filaments and water-filled nanotubes formed by SOD1 mutant proteins linked to familial ALS Nature Struct. Biol. Jun. 2003, p. 461-467, vol. 10, No. 6 Nature Pub. Co., New York, U.S.A.

Jonsson, et al.; Minute quantities of misfolded mutant superoxide disumtase-1 cause amyotrophic lateral sclerosis. Brain. Jan. 2004, pp. 73-88. vol. 127, Oxford Univiersity Press, England.

Urushitani, et al; Chromogranin-mediated secrection of mutant superoxide disumtase proteins linked to amyotrophic lateral sclerosis. Nature Neurosci. Jan. 2006, pp. 108-118, vol. 9, No. 1. Nature Publishing Group, New York, U.S.A.

Sendtner, M: Damaging secretions: chrmogranins team up with mutant SOD 1. Nature Neurosci. Jan. 2006, pp. 12-14, vol. 9, No. 1. Nature Publishing Group, New York, U.S.A.

McCaffrey, P.: SOD1 mutant protein gets loose in ALS. Lancet Neurology, Feb. 2006, p. 119, vol. 5, No. 2. Lancet Publishing Group, New York, U.S.A.

(56) References Cited

OTHER PUBLICATIONS

Griffin, et al.: Isomorphic recruitment of superoxide dismutates in amyotrophic lateral sclerosis, Poster presented at the 13th International Symposium on ALS/MND, Nov. 2002.
Urushitani et al., The endoplasmic reticulum-Golgi pathway is a target for translocation and aggregation of mutant superoxide dismutes linked to ALS, The FASEB Journal vol. 22, pp. 2476-2487, Jul. 2008.
Dunitz M., Session 7A protein folding and degradation effects: function of the proteasome in cell regulation and neuromuscular disease, Amyotrophic Lateral Sclerosis, 2005, 6: 33-35.
Kabashi et al., Oxidized/Misfolded Superoxide Dismutase-1: The Case of All Amyotrophic Lateral Sclerosis? Annals of Neurology 62(6):553-559, Dec. 2007.
Haenggeli et al., Therapeutic immunization with a glatiramer acetate derivative does not alter survival in G93A and G37R SOD1 mouse models of familial ALS. Neurobiology or Disease, 26: 146-152, 2007.
Gruzman et al., Common molecular signature in SOD1 for both sporadic and familial amyotrophic lateral sclerosis PNAS, Jul. 24, 2007, 104(30): 1254-12529, Jul. 16, 2007.
Urushitani et al., Therapeutic effects of immunization with mutant superoxide dismutase in mice models of amyotrophic lateral slcerosis, Proc. Natl. Acad. Sci., Feb. 13, 2007, pp. 2495-2500, vol. 104, No. 7. National Academy of Sciences, D.C., U.S.A.
Vande Velde et al., Selective association of misfolded ALS-linked mutant SOD1 with the cytoplasmic face of mitochondira, PNAS, Mar. 2008, vol. 105, No. 10 pp. 4022-4027.
Hsueh-Ning L., et al. Targeting of Monomer/Misfolded SOD1 as a Therapeutic Strategy for Amyotrophic Lateral Sclerosis. The Journal of Neuroscience, Jun. 27, 2012, 32(26):8791-8799.
Database Geneseq [Online] Feb. 24, 1999, Human Cu/Zn SOD exon 2 protein fragment. XP002681987, retrieved from EBI accession No. GSP:AAW82448. Database accession No. AAW82448.
Fujiwara Noriko et al. Different immunoreactivity against monoclonal antibodies between wild-type and mutant copper/zinc superoxide dismutase linked to amyotrophic lateral sclerosis. Journal of Biological Chemistry, the American Society of Biological Chemists, Inc, US, vol. 280, No. 6, Feb. 11, 2005, pp. 5061-5070.
Kawaguchi T. et al., A Monoclonal Antibody against COOH-terminal Peptide of Human Liver Manganese Superoxide Dismutase. The Journal of Biological Chemistry, vol. 264, Issue fo Apr. 5, pp. 5762-5767, 1989.
Bartlett S.E. et al. Development and characterization of human and mouse specific antibodies to CuZn-superoxide dismutase (SOD1). Journal of Neuroscience Methods, 2000, vol. 98, No. 1, pp. 63-67.
Roberts B. R., et al. Structural Characterization of Zinc-deficient Human Superoxide Dismutase and Implications for ALS. J. Mol. Biol., 2007, vol. 373, pp. 877-890.
Danielsson J. et al. Cutting Off Functional Loops from Homodimeric Enzyme Superoxide Dismutase 1 (SOD1) Leaves Monomeric β-Barrels. The Journal of Biological Chemistry. vol. 286, No. 38, pp. 33070-33063, Sep. 23, 2011.
David F. et al. Absence of a close linkage between Alzheimer's disease and the polymorphic probe coding for superoxide dismutase 1. Acad. Sci., vol. 306, No. 1, pp. 1-4, 1988. Abstract only.
Brody, David L., et al. Active and Passive Immunotherapyy for Neurodegenerative Disorders. Annu. Rev. Neurosci. 2008, vol. 31, pp. 175-193.
U.S. Appl. No. 10/568,729, filed Aug. 20, 2004, Neil Cashman.
U.S. Appl. No. 13/313,869, filed Mar. 3, 2006, Neil Cashman.
U.S. Appl. No. 10/568,729, Dec. 29, 2010, Abandonment.
U.S. Appl. No. 10/568 729, Jun. 22, 2010, Final Rejection.
U.S. Appl. No. 10/568,729, Mar. 29, 2010, Amendment after Non-Final Rejection.
U.S. Appl. No. 10/568,729, Dec. 29, 2009, Non-Final Rejection.
U.S. Appl. No. 10/568,729, Oct. 9, 2009, Amendment after Final and RCE.
U.S. Appl. No. 10/568,729, Sep. 9, 2009, Examiner Interview Summary.
U.S. Appl. No. 10/568,729, Jun. 10, 2009, Final Reiection.
U.S. Appl. No. 10/568,729, Mar. 23, 2009, Response to Non-Final Rejection.
U.S. Appl. No. 10/568,729, Dec. 8, 2008, Non-Final Rejection.
U.S. Appl. No. 10/568,729, Aug. 15, 2008, Response to Restriction Election.
U.S. Appl. No. 10/568,729, Sep. 5, 2007, Preliminary Amendment.
U.S. Appl. No. 10/568,729, Jul. 13, 2006, Preliminary Amendment.
U.S. Appl. No. 10/568,729, Feb. 17, 2006, Preliminary Amendment.
U.S. Pat. No. 7,439,324, Oct. 21, 2008, Recordation of Patent Grant.
U.S. Pat. No. 7,439,324, Oct. 1, 2008, Issue Notification.
U.S. Pat. No. 7,439,324, Sep. 15, 2008, Issue Fee Payment.
U.S. Pat. No. 7,439,324, Jun. 16, 2008, Notice of Allowance.
U.S. Pat. No. 7,439,324, Apr. 16, 2008, Final Rejection.
U.S. Pat. No. 7,439,324, Jan. 24, 2008, Response to Non-Final Action.
U.S. Pat. No. 7,439,324, Oct. 25, 2007, Non-Final Rejection.
U.S. Pat. No. 7,439,324, Apr. 17, 2006, Preliminary Amendment.
U.S. Pat. No. 7,763,710, Jul. 27, 2010, Recordation of Patent Grant.
U.S. Pat. No. 7,763,710, Mar. 1, 2010, Notice of Allowance.
U.S. Pat. No. 7,763,710, Dec. 18, 2009, Response to non-Final Action.
U.S. Pat. No. 7,763,710, Sep. 22, 2009, Non-Final Rejection.
U.S. Pat. No. 7,763,710, Dec. 15, 2008, Preliminary Amendment.
U.S. Pat. No. 8,075,891, Dec. 13, 2011, Recordation of Patent Grant.
U.S. Pat. No. 8,075,891, Aug. 9, 2011, Notice of Allowance.
U.S. Pat. No. 8,075,891, Jun. 13, 2011, Response to Restriction Requirement.
U.S. Pat. No. 8,075,891, May 12, 2011, Restriction Requirement.
U.S. Pat. No. 8,075,891, Aug. 16, 2010, Preliminary Amendment.
Australia, 2004266324, Apr. 21, 2011, Patent Granted.
Australia, 2004266324, Dec. 16, 2010, Application Accepted.
Australia, 2004266324, Dec. 9, 2010, Amendment Filed.
Australia, 2004266324, Nov. 4, 2010, Response to Second Examiner's Report.
Australia, 2004266324, Aug. 16, 2010, Second Examiner's Report.
Australia, 2004266324, Jul. 12, 2010, Response to Office Action.
Australia, 2004266324, Jul. 10, 2009, Office Action.
EP, 04761667.7, Response to Examination Report.
EP, 04761667.7, Sep. 16, 2010, Examination Report.
EP, 04761667.7, Sep. 21, 2009, Supplementary European Search Report and Opinion.
WO, PCT/CA/2004/001503 (WO 2005/019828), Feb. 21, 2006, International Preliminary Opinion on Patentability.
WO, PCT/CA/2004/001503 (WO 2005/019828), Dec. 24, 2004, International Search Report.
CA, 2,437,675, Jan. 19, 2012, Application Abandoned.
CA, 2,437,675, Jul. 9, 2010, Office Action.
CA, 2,437,999, Jan. 16, 2012, Response to OA.
CA, 2,437,999, Jul. 16, 2010, Office Action.
CA, 2,536,305, Jan. 19, 2011, Response to Office Action.
CA, 2,536,305, Jul. 9, 2010, Office Action.
Japan, 2006-523496, Jan. 29, 2011, Patent Granted.
Japan, 2006-523496, Oct. 20, 2010, Response to Second Office Action.
Japan, 2006-523496, Jul. 27, 2010, Second Office Action.
Japan, 2006-523496, Jul. 5, 2010, Response to Office Action.
Japan, 2006-523496, May 1, 2010, Office Action.
Japan, 2010-153006, Feb. 16, 2011, Response to Office Action.
Japan, 2010-153006, Jan. 18, 2011, Office Action.
U.S. Appl. No. 11/367,609, Oct. 21, 2008, Recordation of Patent Grant.
U.S. Appl. No. 11/367,609, Oct. 1, 2008, Issue Notification.
U.S. Appl. No. 11/367,609, Sep. 15, 2008, Issue Fee Payment.
U.S. Appl. No. 11/367,609, Jun. 16, 2008, Notice of Allowance.
U.S. Appl. No. 11/367,609, Apr. 16, 2008, Final Rejection.
U.S. Appl. No. 11/367,609, Jan. 24, 2008, Response to Non-Final Action.
U.S. Appl. No. 11/367,609, Oct. 25, 2007, Non-Final Rejection.
U.S. Appl. No. 11/367,609, Apr. 17, 2006, Preliminary Amendment.
U.S. Appl. No. 11/565,967, Sep. 14, 2010, Recordation of Patent Grant.

(56) References Cited

OTHER PUBLICATIONS

U.S. Appl. No. 11/565,967, Aug. 25, 2010, Issue Notification.
U.S. Appl. No. 11/565,967, Jul. 19, 2010, Issue Fee Payment.
U.S. Appl. No. 11/565,967, Apr. 19, 2010, Notice of Allowance.
U.S. Appl. No. 11/565,967, Apr. 19, 2010, Applicant Summary of Interview with Examiner.
U.S. Appl. No. 11/565,967, Mar. 25, 2010, Examiner Interview Summary.
U.S. Appl. No. 11/565,967, Mar. 24, 2010, Amendment after Final.
U.S. Appl. No. 11/565,967, Nov. 25, 2009, Final Rejection.
U.S. Appl. No. 11/565,967, Oct. 14, 2009, Supplemental Response.
U.S. Appl. No. 11/565,967, Oct. 2, 2009, Interview Summary.
U.S. Appl. No. 11/565,967, Sep. 8, 2009, Response to Non-Final Action.
U.S. Appl. No. 11/565,967, Apr. 7, 2009, Non-Final Office Action.
U.S. Appl. No. 11/565,967, Jun. 13, 2008, Response to non-Final Action.
U.S. Appl. No. 11/682,217, Jul. 12, 2011, Recordation of Patent Grant.
U.S. Appl. No. 11/682,217, Jun. 22, 2011, Issue Notification.
U.S. Appl. No. 11/682,217, Mar. 3, 2011, Notice of Allowance.
U.S. Appl. No. 11/682,217, Oct. 14, 2010, Response to Non-Final Rejection.
U.S. Appl. No. 11/682,217, Jul. 14, 2010, Non-Final Rejection.
U.S. Appl. No. 11/682,217, Apr. 30, 2010, Response to Restriction Election.
U.S. Appl. No. 11/682,217, Mar. 5, 2010, Requirement for Restriction Election.
U.S. Appl. No. 11/682,217, Oct. 2, 2009, Applicant Summary of Interview with Examiner.
U.S. Appl. No. 11/682,217, May 11, 2009, Preliminary Amendment.
U.S. Appl. No. 11/682,217, Jan. 29, 2009, Response to Non-Final Rejection.
U.S. Appl. No. 11/682,217, Oct. 29, 2008, Non-Final Rejection.
U.S. Appl. No. 11/682,217, Feb. 14, 2008, Response to Restriction Election.
U.S. Appl. No. 11/682,217, Jan. 14, 2008, Requirement for Restriction Election.
U.S. Appl. No. 11/682,217, Aug. 20, 2007, Preliminary Amendment.
U.S. Appl. No. 11/682,217, Jun. 28, 2007, Preliminary Amendment.
U.S. Appl. No. 11/850,502, Feb. 15, 2011, Recordation of Patent Grant.
U.S. Appl. No. 11/850,502, Jan. 26, 2010, Issue Notification.
U.S. Appl. No. 11/850,502, Dec. 24, 2010, Issue Fee Payment.
U.S. Appl. No. 11/850,502, Sep. 30, 2010, Notice of Allowance.
U.S. Appl. No. 11/850,502, Aug. 24, 2010, Response to Final Rejection.
U.S. Appl. No. 11/850,502, May 26, 2010, Final Rejection.
U.S. Appl. No. 11/850,502, Feb. 19, 2010, Amendments after Non-Final Rejection.
U.S. Appl. No. 11/850,502, Oct. 19, 2009, Non-Final Rejection.
U.S. Appl. No. 11/850,502, Jul. 29, 2008, Preliminary Amendment.
U.S. Appl. No. 11/850,502, Jul. 2, 2008, Preliminary Amendment.
U.S. Appl. No. 11/850,502, Jan. 7, 2008, Preliminary Amendment.
U.S. Appl. No. 12/236,731, Jul. 27, 2010, Recordation of Patent Grant.
U.S. Appl. No. 12/236,731, Jul. 7, 2010, Issue Notification.
U.S. Appl. No. 12/236,731, Jun. 1, 2010, Issue Fee Payment.
U.S. Appl. No. 12/236,731, Mar. 1, 2010, Notice of Allowance.
U.S. Appl. No. 12/236,731, Dec. 18, 2009, Response to non-Final Action.
U.S. Appl. No. 12/236,731, Sep. 22, 2009, Non-Final Rejection.
U.S. Appl. No. 12/236,731, Dec. 15, 2008, Preliminary Amendment.
U.S. Appl. No. 12/792,394, Dec. 13, 2011, Recordation of Patent Grant.
U.S. Appl. No. 12/792,394, Nov. 22, 2011, Issue Notification.
U.S. Appl. No. 12/792,394, Aug. 9, 2011, Notice of Allowance.
U.S. Appl. No. 12/792,394, Jun. 13, 2011, Response to Restriction Requirement.
U.S. Appl. No. 12/792,394, May 12, 2011, Restriction Requirement.
U.S. Appl. No. 12/792,394, Aug. 16, 2010, Preliminary Amendment.
U.S. Appl. No. 12/840,708, Aug. 20, 2013, Recordation of Patent Grant.
U.S. Appl. No. 12/840,708, Jul. 31, 2013, Issue Notification.
U.S. Appl. No. 12/840,708, Apr. 23, 2013, Notice of Allowance.
U.S. Appl. No. 12/840,708, Mar. 18, 2013, Voluntary Amendment and Response.
U.S. Appl. No. 12/840,708, Mar. 12, 2013, Final Rejection.
U.S. Appl. No. 12/840,708, Nov. 8, 2012, Response to Non-Final Rejection.
U.S. Appl. No. 12/840,708, Aug. 8, 2012, Non-Final Rejection.
U.S. Appl. No. 12/840,708, Jun. 15, 2012, Response to Restriction Requirement.
U.S. Appl. No. 12/840,708, Apr. 20, 2012, Restriciton Requirement.
U.S. Appl. No. 12/840,708, Oct. 1, 2010, Preliminary Amendment.
U.S. Appl. No. 12/978,478, Dec. 4, 2013, Notice of Allowance.
U.S. Appl. No. 12/978,478, Nov. 8, 2013, Response to Final Rejection.
U.S. Appl. No. 12/978,478, Jul. 8, 2013, Final Rejection.
U.S. Appl. No. 12/978,478, Apr. 4, 2013, Response to Non-Final Rejection.
U.S. Appl. No. 12/978,478, Dec. 4, 2012, Non-Final Rejection.
U.S. Appl. No. 12/978,478, Jul. 23, 2012, Response to Restriction Requirement.
U.S. Appl. No. 12/978,478, May 22, 2012, Restriction Requirement.
U.S. Appl. No. 13/155,939, May 23, 2013, Response to Non-final Rejection.
U.S. Appl. No. 13/155,939, May 23, 2013, Non-Final Rejection.
U.S. Appl. No. 13/155,939, Apr. 26, 2013, Response to Final Rejection.
U.S. Appl. No. 13/155,939, Jan. 31, 2013, Final Rejection.
U.S. Appl. No. 13/155,939, Nov. 19, 2012, Response to Non-Final Rejection.
U.S. Appl. No. 13/155,939, Jun. 18, 2012, Non-Final Rejection.
U.S. Appl. No. 13/155,939, Mar. 9, 2012, Response to Restriction Requirement.
U.S. Appl. No. 13/155,939, Feb. 9, 2012, Restriction Requirement.
U.S. Appl. No. 13/155,939, Aug. 26, 2011, Preliminary Amendment.
U.S. Appl. No. 13/313,869, Nov. 22, 2013, Non-Final Rejection.
U.S. Appl. No. 13/313,869, Mar. 6, 2013, Preliminary Amendment.
Australia, 2007219615, Nov. 18, 2013, Notice of Acceptance.
Australia, 2007219615, Oct. 22, 2013, Response to Second Office Action.
Australia, 2007219615, Jun. 13, 2013, Second Office Action.
Australia, 2007219615, May 22, 2013, Response to Office Action.
Australia, 2007219615, May 22, 2012, Office Action.
EP, 07710682.1, Jan. 14, 2014, Noting of Loss of Rights.
EP, 07710682.1, Jun. 5 2013, Third Examination Report.
EP, 07710682.1, Sep. 21, 2012, Response to Examination Report.
EP, 07710682.1, Jun. 14, 2012, Rejection of Request of Extension of Time.
EP, 07710682.1, Nov. 30, 2011, Second Examination Report.
EP, 07710682.1, Jan. 14, 2011, Response to Examination Report.
EP, 07710682.1, Mar. 17, 2010, Examination Report.
EP, 07710682.1, Nov. 26, 2009, Supplementary European Search Report and Opinion.
EP, 07710682.1, Nov. 18, 2008, Amended Claims.
EP, 04761667.7, Dec. 5, 2012, Response to Second ER.
EP, 04761667.7, May 29, 2012, Second Examination Report.
EP, 12161564.5, Sep. 13, 2013, Examination Report.
EP, 12161564.5, Jul. 30, 2013, Response to EESR.
EP, 12161564.5, Jan. 2, 2013, Full European Search Report.
EP, 12161564.5, Sep. 5, 2012, Partial European Search Report.
EP, 12161568.6, Oct. 22, 2013, Examination Report.
EP, 12161568.6, Jul. 23, 2013, Response to EESR.
EP, 12161568.6, Jan. 2, 2013, Full European Search Report.
EP, 12161568.6, Sep. 5, 2012, Partial European Search Report.
EP, 12161571.0, Oct. 23, 2013, Examination Report.

(56) References Cited

OTHER PUBLICATIONS

EP, 12161571.0, Jul. 23, 2013, Response to EESR.
EP, 12161571.0, Jan. 2, 2013, Full European Search Report.
EP, 12161571.0, Aug. 27, 2012, Partial European Search Report.
EP, 12161575.1, Jan. 14, 2014, Noting of loss of rights.
EP, 12161575.1, Jun. 6, 2013, Examination Report.
EP, 12161575.1, Apr. 17, 2013, Response to EESR.
EP, 12161575.1, Sep. 17, 2012, Extended European Search Report.
WO, PCT/CA2007/000346 (WO2007/098607), Jun. 27, 2008, International Preliminary Report on Patentability.
WO, PCT/CA2007/000346 (WO2007/098607), Jul. 26, 2007, International Search Report.
WO, PCT/CA2009/000930 (WO 2010/003227), Jan. 20, 2011, International Preliminary Report on Patentability.
WO, PCT/CA2009/000930 (WO 2010/003227), Nov. 2, 2009, International Search Report and Opinion.
CA, 2,437,999, Oct. 8, 2013, Recordation of Patent Grant.
CA, 2,437,999, Apr. 2, 2013, Notice of Allowance.
CA, 2,437,999, Feb. 28, 2013, Response to Second OA.
CA, 2,437,999, Aug. 31, 2012, Second Office Action.
CA, 2,437,999, Jan. 3, 2012, Notice of Reinstatement.
CA, 2,437,999, Dec. 19, 2011, Response to OA and Request for Reinstatement.
CA, 2,437,999, Apr. 11, 2011, Notice of Abandonment.
CA, 2,536,305, Oct. 23, 2013, Fourth Office Action.
CA, 2,536,305, Feb. 14, 2013, Response to Third OA.
CA, 2,536,305, Aug. 14, 2012, Third Office Action.
CA, 2,536,305, Jul. 20, 2012, Response to Second OA.
CA, 2,536,305, Feb. 2, 2012, Second Office Action.
CA, 2,642,848, May 14, 2013, Response to Office Action.
CA, 2,642,848, Nov. 14, 2012, Second Office Action.
CA, 2,642,848, Oct. 14, 2011, Response to Office Action.
CA, 2,642,848, Apr. 14, 2011, Office Action.
Japan, 2010-153006, Sep. 6, 2013, Certificate of Patent.
Japan, 2010-153006, Jul. 30, 2013, Notice of Allowance.
Japan, 2010-153006, Mar. 13, 2013, Response to Office Action.
Japan, 2010-153006, Dec. 18, 2012, Second Office Action.
Japan, 2008-556626, Oct. 30, 2013, Decision of Rejection.
Japan, 2008-556626, May 16, 2013, Response to Office Action.
Japan, 2008-556626, Jan. 21, 2013, Second Office Action.
Japan, 2008-556626, Dec. 18, 2012, Response to Office Action.
Japan, 2008-556626, Jun. 18, 2012, Office Action.
Japan, 2008-556626, Mar. 2, 2010, Amendment.
Japan, 2008-556626, Feb. 26, 2014, Office Action.
Fujisawa T. et al. A Novel Monoclonal Antibody Reveals a Conformational Alteration Shared by Amyotrophic Lateral Sclerosis-Linked SOD1 Mutants, Ann Neurol 2012;72:739-749.
Hough, Michael A. et al. Dimer destabilization in superoxide dismutase may result in disease-causing properties: Structures of motor neuron disease mutants. PNAS, Apr. 20, 2004, pp. 59-76-5981, vol. 101, No. 16.
Bruijn L. et al., ALS-linked SOD1 mutant G85R mediates damage to astrocytes and promotes rapidly progressive disease with SOD1-containing inclusions, Neuron 1997, vol. 18(2):327-338.
Otvos et al. Curr. Protein Pept. Sci. 2002, Dec. 3; 643-652.
Johnston et al., PNAS, 97(23):12571-12576, Nov. 2000.
Kunst et al., Nature Genetics, 15:91-94, 1997.
Product No. S-2147 Product Information Sheet [online] published Aug. 1998.
UniProtKB/Swiss-Prot entry P00441, SODC_Human, Jul. 21, 1986.
Harris et al., Micron, 30:597-623, Dec. 1999.
Bolton et al., Molecular location of a species-specific epitope on the hamster scrapie agent protein. Jul. 1991. Journal of Virology, vol. 65, No. 7, pp. 3667-3675.
Pardo, Carlos et al., Superoxide dismutase is an abundant component in cell bodies, dendrites, and axons of motor neurons and in a subset of other neurons, Proc. Natl. Acad. Sci., Feb. 1995, vol. 92, pp. 954-958.
Safar et al., Measuring prions causing bovine spongiform encephalopathy or chronic wasting disease by immunoassays and transgenic mice, Nov. 2002, Nat. Biotechnol., 20(11):1147-1150.
Paramithiotitis et al. A prion protein epitope selective for the pathologically misfolded conformation, Jul. 2003, Nat. Med.m 9(7):893-899.
Soto C., Diagnosing prion diseases: needs, challenges and hopes, Oct. 2004, Nature Rev Microbiol., 2 (10):809-819.
Kim et al., Free Rad. Biol. Med. 2002. 32:544-550.
Burgess et al., J of Cell Bio. 1990, 111:2129-2138.
Bowie et al., Science 1990, 247:1306-1310.
Pawson et al., 2003, Science, 300:445-452.
Lehto, M.T. et al., Society for Neuroscience Annual Meeting; Nov. 2-7, 2002; Peroxynitrite as a Probe for the Structure of Normal and Misfolded Prion Protein. Program No. 692.9, Poster.
Lehto, M.T. et al., Society for Neuroscience Annual Meeting; Aug. 21, 2002, Peroxynitrite as a Probe for the Structure of Normal and Misfolded Prion Protein, Program No. 692.9, Abstract.

* cited by examiner

A

B

FIGURE 4 – CONTINUED
B
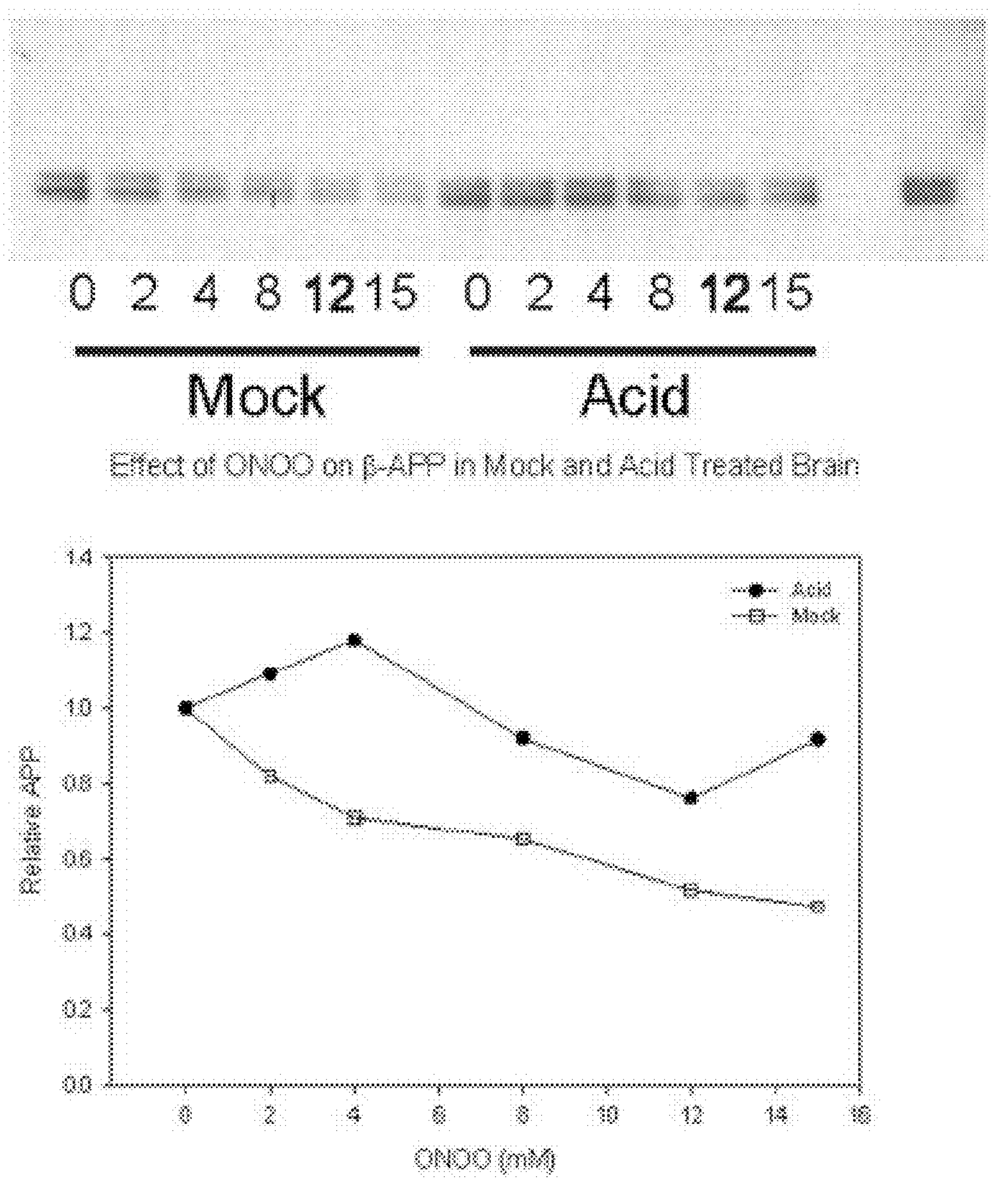

FIGURE 4 – CONTINUED
C
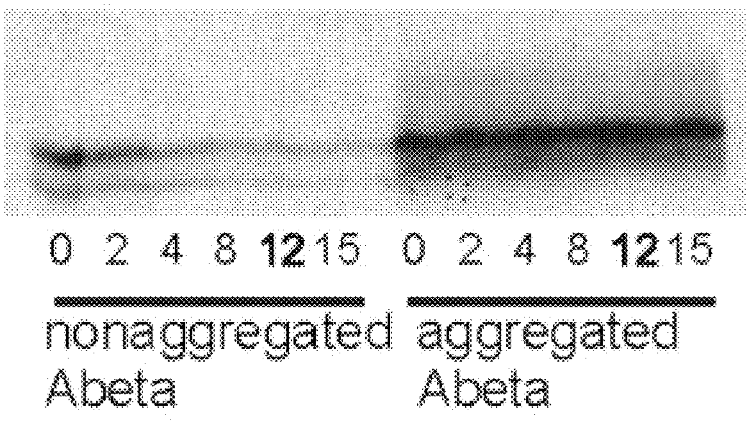
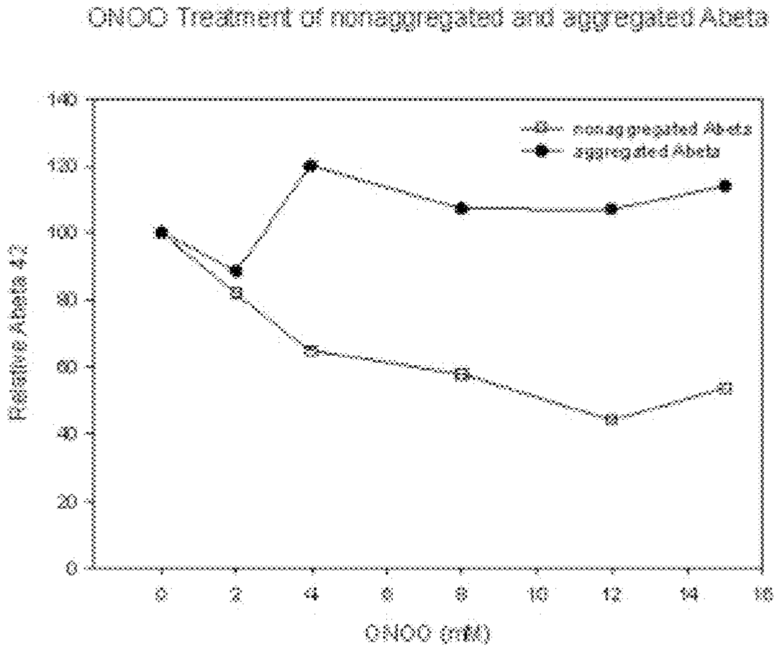

FIGURE 4- CONTINUED
D
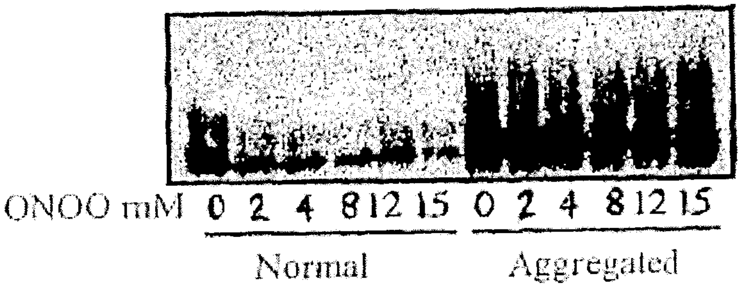
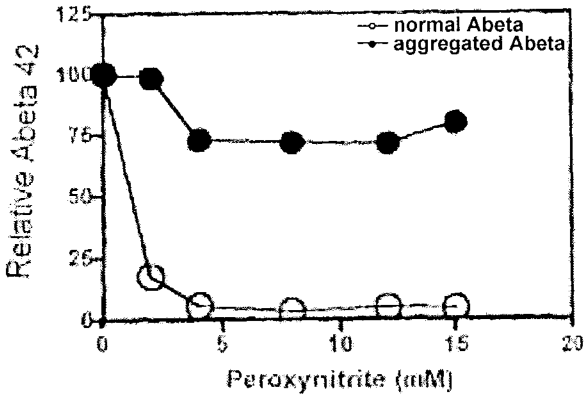

A

B

A

| 0 0.1µM 1µM 10µM 100µM 1mM 10mM | 0 0.1µM 1µM 10µM 100µM 1mM 10mM |
|---|---|
| Normal α-synuclein | Insoluble α-synuclein |

B

SEQUENCE LISTING

```
<160> NUMBER OF SEQ ID NOS: 10

<210> SEQ ID NO 1
<211> LENGTH: 4
<212> TYPE: PRT
<213> ORGANISM: Artificial sequence
<220> FEATURE:
<223> OTHER INFORMATION: epitope

<400> SEQUENCE: 1

Met Lys His Met
1


<210> SEQ ID NO 2
<211> LENGTH: 9
<212> TYPE: PRT
<213> ORGANISM: Artificial sequence
<220> FEATURE:
<223> OTHER INFORMATION: epitope
```

<400> SEQUENCE: 2

Asp Tyr Glu Asp Arg Tyr Tyr Arg Glu
1 5

<210> SEQ ID NO 3
<211> LENGTH: 6
<212> TYPE: PRT
<213> ORGANISM: Artificial sequence
<220> FEATURE:
<223> OTHER INFORMATION: epitope

<400> SEQUENCE: 3

Glu Phe Arg His Asp Ser
1 5

<210> SEQ ID NO 4
<211> LENGTH: 6
<212> TYPE: PRT
<213> ORGANISM: Homo sapiens

<400> SEQUENCE: 4

Gln Lys Glu Ser Asn Gly
1 5

<210> SEQ ID NO 5
<211> LENGTH: 10
<212> TYPE: PRT
<213> ORGANISM: Homo sapiens

<400> SEQUENCE: 5

Glu Asp Asn Thr Ala Gly Cys Thr Ser Ala
1 5 10

<210> SEQ ID NO 6
<211> LENGTH: 8
<212> TYPE: PRT
<213> ORGANISM: Homo sapiens

<400> SEQUENCE: 6

Pro Lys Asp Glu Glu Arg His Val
1 5

<210> SEQ ID NO 7
<211> LENGTH: 5
<212> TYPE: PRT
<213> ORGANISM: Homo sapiens

<400> SEQUENCE: 7

Ala Asp Lys Asp Gly
1 5

<210> SEQ ID NO 8
<211> LENGTH: 10
<212> TYPE: PRT
<213> ORGANISM: Homo sapiens

<400> SEQUENCE: 8

Gly Lys Gly Gly Asn Glu Gln Ser Thr Lys
1 5 10

<210> SEQ ID NO 9
<211> LENGTH: 18
<212> TYPE: PRT
<213> ORGANISM: Homo sapiens

-continued

```
<400> SEQUENCE: 9

Asp Leu Gly Lys Gly Gly Asn Glu Glu Ser Thr Lys Thr Gly Asn Ala
1               5                   10                  15

Gly Ser


<210> SEQ ID NO 10
<211> LENGTH: 14
<212> TYPE: PRT
<213> ORGANISM: Homo sapiens

<400> SEQUENCE: 10

Asn Pro Leu Ser Arg Lys His Gly Gly Pro Lys Asp Glu Glu
1               5                   10
```

DETECTION OF PATHOGENIC ABETA USING AN EPITOPE PROTECTION ASSAY

This application is a continuation of U.S. patent application Ser. No. 10/568,729 filed Jul. 13, 2006, which is a National stage entry of International Application No. PCT/CA2004/001503, filed Aug. 20, 2004, which claims priority to U.S. Provisional Application No. 60/496,381, filed Aug. 20, 2003, Canadian Application No. 2,437,675, filed Aug. 20, 2003, U.S. Provisional Application No. 60/497,362, filed Aug. 21, 2003 and Canadian Application No. 2,437,999 filed Aug. 21, 2003, the disclosures of each of which are incorporated herein by reference.

INCORPORATION OF SEQUENCE LISTING

A computer readable form of the Sequence Listing "15289-36_SequenceListing.txt" (2071 bytes), created Oct. 22, 2010, is herein incorporated by reference.

FIELD OF THE INVENTION

The invention relates to an epitope protection assay for use in diagnosis, prognosis and therapeutic intervention in diseases, for example, diseases involving polypeptide aggregation such as prion infections.

BACKGROUND OF THE INVENTION

Protein Misfolding and Aggregation

Proteins can fold into complex and close-packed structures. Folding is not only crucial for biological activity but failure of proteins to fold properly or remain folded can give rise to disease (Dobson C M, Methods (2004) 34:4-14). Misfolding can in some cases cause protein aggregation which can further give rise to discrete deposits extracellularly (e.g., plaques) or intracellularly (e.g., inclusions in the cytosol or nucleus).

Neurogenerative diseases such as Alzheimer's disease (AD), Parkinson's disease (PD), Huntington's disease (HD), amyotrophic lateral sclerosis (ALS) and prion diseases are characterized by neural deposits of misfolded aggregated protein. Type II diabetes and cancer have also been linked to protein misfolding and it is likely that there are yet to be identified diseases that result from errors in protein folding and that in some cases lead to consequences such as aggregation. The nature of the misfolding and any aggregation in such diseases is typically not well characterized.

Prion Diseases

Prion diseases have become a major health concern since the outbreak of BSE or "Mad Cow Disease" (reviewed above, 40, 41). BSE was first discovered in the United Kingdom but has now spread to many other countries in Europe and Japan. In the UK alone there has been close to 180,000 cases of BSE, which resulted in the destruction of cattle and possible infection of an estimated 3-5 million head. The total cost estimated to the UK was in excess of $2.5 billion. BSE is believed to be transmitted among cattle through feed that contains prions rendered from infected cattle, and it is thought to be transmitted to humans through eating beef or other cattle products from infected animals.

Emerging Prion Diseases

The prion diseases are a group of rapidly progressive and untreatable neurodegenerative syndromes, neuropathologically characterized by spongiform change, neuronal cell loss, gliosis, and brain accumulation of abnormal amyloid polypeptide. Human prion diseases include classical Creutzfeldt-Jakob disease (CJD), which has sporadic, iatrogenic, and familial forms. Since 1996, a "new variant" of CJD (vCJD) has been identified in the United Kingdom, France, the Republic of Ireland, Hong Kong, Italy, the United States, and Canada (40,41). Variant CJD is capable of killing individuals as young as age 14 with unknown incubation period. There is little doubt that vCJD is a human form of bovine spongiform encephalopathy (BSE) (42). The primary epidemic from consumption of contaminated cattle tissue has affected over 130 individuals as of this filing.

The spectre of vCJD "secondary epidemics" through blood, blood products, surgery, dentistry, vaccines, and cosmetics is of great concern (40,41). Detection of blood prion infectivity in experimental BSE/vCJD infections of mice and sheep (40) suggests a special risk exists for the transmission of vCJD through blood and blood products. The recent reports of vCJD in two recipients of a donor who developed the disease is also troubling (52, 53). Canada and the United States have recently expanded vCJD blood donor deferrals to all countries in Western Europe.

Although sheep scrapie has been known for centuries, the most important animal prion disease at present is BSE. More than 173,000 cattle, primarily from Britain, have developed symptomatic BSE, and as many as 3 million have entered the food supply undetected. BSE is now being increasingly reported in cattle which were "born after the ban" in 1996 of food supplementation with meat and bone meal, suggesting that alternate routes may exist to keep the epidemic from being readily extinguished. Another troubling issue is the possible transmission of BSE to sheep, which may expose additional human populations to the BSE/vCJD prion strain. Recent reports show that prions can replicate in certain muscle groups of sheep, experimental animals and humans (54-57), indicating a potential risk in tissues previously considered safe for human consumption.

Chronic wasting disease (CWD) of captive and wild cervids (deer and elk) represents another newly emergent animal prion disease in North America, whose impact on human health is yet unknown. It is apparent that newly-recognized prion diseases pose a threat to the safety of foods, blood products, and medical-surgical treatments.

Prions: Atypical Pathogens

Newly emergent prion diseases, and the polypeptide-only nature of prions, have created serious medical, veterinary, and economic challenges worldwide. To date, the only commercialised tests for prion infection have been based on post-mortem brain samples. No biochemical test exists to detect prions in the blood of infected animals, despite detection by experimental transmission studies. The development of sensitive and specific diagnostic tests for prion infection is a challenging task, in part due to the unusual nature of the prion infectious agent. The infectious agents that transmit the prion diseases differ from other pathogens in that no nucleic acid component has been detected in infectious materials (41). According to the prion theory developed by Nobel Laureate Dr. Stanley Prusiner, infectivity resides in $PrP^{Sc}$, a misfolded conformational isoform of the near-ubiquitous normal cellular prion polypeptide $PrP^{C}$. $PrP^{Sc}$ is indeed the most prominent (or perhaps sole) macromolecule in preparations of prion infectivity, and minimally appears to be a reliable surrogate for prion infection. $PrP^{Sc}$ is partially resistant to protease digestion, poorly soluble, and exists in an aggregated state, in contrast to the protease sensitive, soluble, monomeric isoform $PrP^{C}$ (29, 31, 43-46).

$PrP^{Sc}$ is derived from its normal cellular isoform ($PrP^C$), which is rich in α-helical structure, by a posttranslational process involving a conformational transition. While the primary structure of $PrP^C$ is identical to that of $PrP^{Sc}$, secondary and tertiary structural changes are responsible for the distinct physicochemical properties of the two isoforms.

One of the difficulties in assessing the safety of food or blood products from potentially infected humans with prions is the lack of an accurate diagnostic test for blood or other accessible biosamples. Currently, there are no diagnostic tests that can be applied for screening live animals, humans, blood or blood products at an early stage. This also provides a further problem in organ transplantation, adding unknown risk to organ recipients. Therefore, as a preventative measure, countries such as the UK no longer source plasma from its inhabitants. The risk of spreading prion diseases has affected other countries as well. For example, the United States and Canada do not accept blood donations from individuals who have resided in the UK or France for more than 3-6 months.

Currently, the diagnosis of vCJD can only be confirmed following pathological examination of the brain at autopsy or biopsy. Some complimentary strategies in early CJD detection include electroencephalograms (EEG), magnetic resonance imaging (MRI) scans, and cerebrospinal fluid (CSF) tests, which may be useful "surrogate" or "proxy" markers. The absence of a "direct test" for prion infection stands in stark contrast to conventional infectious agents, such as viruses and bacteria.

Some tests that are in the process of being commercialized are based on surrogate markers of infection which are "once removed" from actual infectious prions.

PrP protease resistance is the basis of most commercially available diagnostic tests for prion disease. In the current methodologies, a sample of brain is removed and digested with proteases that can eliminate $PrP^C$, but leave a protease-resistant core of $PrP^{Sc}$. The protease-resistant fragment of $PrP^{Sc}$ is then detected by immunoblotting (as in the Prionics test) or by capture ELISA (as in the BioRad and Enfer tests, and in a new test from Prionics). However, digestion with proteases is cumbersome and variable, leading to false negatives and positives. Moreover, there are some prion strains which are reported to contain $PrP^{Sc}$ which is infectious and aggregated, but which is not protease resistant. Protease-sensitive $PrP^{Sc}$ also predominates early in infection and in cross-species transmission of disease (31).

Detection of protease-resistant PrP fragments is also the basis of a urine diagnostic test (47) which is being commercially developed by Prionics. However, detection of protease-resistant PrP in urine is subject to the same limitations as the post-mortem brain test, and has the additional disadvantage of requiring precipitation from large volumes of urine, and poor sensitivity (for example, only detecting $PrP^{Sc}$ in late stages of the disease, not pre-symptomatically).

Other Neurodegenerative Diseases

Neurodegenerative diseases, such as Alzheimer's disease (AD), Huntington's disease, amyotrophic lateral sclerosis (ALS) and Parkinson's disease/Lewy body dementia (PD, LBD) also pose major challenges to our aging population and health care system (reviewed in 1). An estimated 364,000 Canadians over 65 are currently diagnosed with AD or a related dementia. With increased life expectancy, the incidence of neurodegenerative disease is expected to grow. By 2025, AD will affect as many as a million Canadians, and by 2050, this number will double.

Sporadic AD, ALS, and PD/LBD are all associated with neural accumulation of pathological multimers of misfolded polypeptides (these could potentially be fibrils, protofilaments, and amorphous aggregates), including the amyloid-beta (Abeta) fragment of the amyloid precursor protein (APP) in AD; superoxide dismutase-1 (SOD1) in ALS, and alpha-synuclein in PD and LBD (1). Additionally familial amyloidotic polyneuropathy (FAP) results from the aggregation of transthyretin to form amyloid deposits. As with prion diseases, mutations in genes encoding these polypeptides are associated with autosomal dominant familial forms of AD, ALS, and PD.

Alzheimer's Disease

AD is a common dementing (disordered memory and cognition) neurodegenerative disease associated with brain accumulation of extracellular plaques composed predominantly of the Abeta (1-40), Abeta (1-42) and Abeta (1-43) peptides, all of which are proteolytic products of APP (reviewed in 4). In addition, neurofibrillary tangles, composed principally of abnormally phosphorylated tau protein (a neuronal microtubule-associated protein), accumulate intracellularly in dying neurons (4). Familial forms of AD can be caused by mutations in the APP gene, or in the presenilin 1 or 2 genes, the protein products of which are implicated in the processing of APP to Abeta. Apolipoprotein E allelic variants also influence the age at onset of both sporadic and familial forms of AD (reviewed in 5). Abeta has been detected in the blood and CSF of AD patients and in normal controls (6). Abeta is also present in vascular and plaque amyloid filaments in trisomy 21 (Down's syndrome), hereditary cerebral hemorrhage with amyloidosis (HCHWA)-Dutch type, and normal brain aging (Mori, H et al. JBC (1992) 267: 17082-86). Tau and phosphorylated tau have been detected in the cerebral spinal fluid (CSF) of AD patients and patients with other neurological diseases (7; reviewed in 8).

Amyotrophic Lateral Sclerosis

ALS is a fatal neuromuscular disease, with an incidence of 1 in 1000 adults, presenting as progressive weakness, muscle atrophy, and spasticity, which is due to degeneration of ~500,000 "lower motor neurons" in the spinal cord and brainstem, and innumerable "upper motor neurons" in the brain cortex. An important clue to the etiology of ALS came with the finding that about 20% of familial ALS (fALS) cases are due to mutations in superoxide dismutase-1 (SOD1) (10,11), a free radical defense enzyme. Over 100 fALS SOD1 missense, nonsense, and intronic splice-disrupting mutations have been catalogued to date (12). Transgenic mice expressing mutant human SOD1 (mtHuSOD1) develop a motor neuron syndrome with clinical and pathological similarities to human ALS (13, 14), whereas mice expressing wild-type human SOD1 (wtHuSOD1) do not develop disease (13). SOD1-containing cytoplasmic inclusions can be detected in many diseased motor neurons from familial and sporadic ALS patients (15), and in most transgenic mouse (16, 17) and tissue culture (18) models of the disease.

Parkinson's and Lewy Body Disease

PD is a neurodegenerative movement disorder second only to AD in prevalence (~350 per 100,000 population; 1). It is clinically characterized by rigidity, slowness of movement, and tremor (reviewed in 21). Most cases of Parkinson's disease are sporadic, but both sporadic and familial forms of the disease are characterized by intracellular Lewy bodies in dying neurons of the substantia nigra, a population of midbrain neurons (~60,000) that are selectively decimated in PD. Lewy bodies are predominantly composed of alpha-synuclein (22). Mutations in the gene encoding alpha-synuclein have been found in patients with familial Parkinson's disease (reviewed in 23). Another gene associated with autosomal recessive PD is parkin, which is involved in alpha-synuclein degradation (22, 23). Diffuse cortical Lewy bodies composed of alpha-synuclein are observed in Lewy body disease (LBD), a dementing syndrome associated with parkinsonian tone changes, hallucinations, and rapid symptom fluctuation (24). LBD may be the second most common form of neurodegenerative dementia after AD, accounting for 20 to 30 percent of cases among persons over the age of 60 years (1, 24).

Huntington's Disease and Related Diseases

HD is a progressive neurodegenerative disorder characterized by expansion of polyglutamine encoding CAG repeats in the N-terminus of the huntingtin protein (reviewed in 48). Polyglutamine stretches of ≥36 cause disease and longer repeats cause earlier onset (49, 50).

Other polyglutamine diseases such as dentate-rubral and pallido-luysian atrophy (DRPLA) and some forms of sinocerebellar ataxia (SCA) also have intracellular inclusions that roughly correlate to regions of neuronal death. Interruptions in the expanded polyglutamine repeat in the SCA-1 gene product result in the absence of disease (51), Neurodegenerative diseases, such as Alzheimer's disease (AD), amyotrophic lateral sclerosis (ALS) and Parkinson's disease/Lewy body disease (PD, LBD) pose major challenges to our aging population and health care system. No specific biochemical test exists for neurodegenerative diseases as a group (1,2). Since neurodegenerative diseases are regarded as "diagnoses of exclusion," very broad investigation is required to achieve "clinically probable" diagnosis for these progressive, incurable, and usually fatal conditions. Expensive surrogate testing, such as neuroimaging, is utilized to increase diagnostic probability (2). The availability of specific, sensitive, and inexpensive biochemical tests for this devastating group of diseases could potentially conserve financial resources for over-burdened health care systems. Moreover, secure diagnosis of these diseases at an earlier symptomatic stage increases the window for enhanced treatment efficacy at a time at which the disease pathophysiology is generally more responsive to treatment (3).

Effective, efficient and inexpensive diagnostic and screening strategies for antemortem diagnosis of human neurodegenerative diseases are urgently needed, given the aging population and continued financial pressure on the health care system.

Diabetes

Protein aggregation is also observed in patients with type II diabetes. Increased expression of the adipocyte-derived peptide, resistin, has been observed in diabetes type II patients (Youn B S et al. J Clin Endocrinol Metab. (2004); 89:150-6) and studies suggest that elevated resistin levels may play a role in obesity and insulin resistance. Additionally, islet amyloid polypeptide (also known as amylin) deposition is pathogenically associated with type 2 diabetes. These deposits contain islet amyloid polypeptide, a unique amyloidogenic peptide and are associated with beta cell death. Recent studies suggest that the species responsible for islet amyloid-induced beta-cell death are formed early in islet amyloid formation, when islet amyloid polypeptide accumulation begins (Hull R L et al. J Clin Endocrinol Metab. (2004) 89:3629-43). A diagnostic test that can identify pathogenic islet amyloid polypeptide would be very useful for detecting type 2 diabetes in its early stages, when dietary and therapeutic interventions are most effective.

Cancer

Many forms of cancer are also considered to be protein conformation diseases (Ishimaru D. et al. Biochemistry (2003) 42:9022-7). A subset of neuroblastomas, carcinomas and myelomas show an abnormal accumulation of tumor suppressor p53 protein aggregates (Butler J S et al. Biochemistry (2003) 42: 2396-403; Ishimaru D. et al. Biochemistry (2003) 42:9022-7). This accumulation could contribute to the loss of p53 function in some cancerous cells (Ishimaru D. et al. Biochemistry (2003) 42:9022-7). Assays able to detect accumulated p53 could provide a diagnostically useful detection system and could enhance therapeutic intervention by individualizing therapeutic intervention.

SUMMARY OF THE INVENTION

The inventors have recently developed the epitope protection assay (EPA), a novel method that yields sensitive and specific antemortem detection of disease proteins in blood and other accessible tissues and fluids. The invention shows the role of aggregation in diseases, such as prion disease, and provides an assay that overcomes problems in the prior art. In prion diseases, the normal cellular monomeric prion polypeptide $PrP^C$ undergoes refolding to an abnormal, aggregated isoform, generically designated $PrP^{Sc}$. Diseases such as AD, PD, LBD, ALS and HD are also characterized by misfolded and/or aggregated conformations of cellular proteins. This property is exploited by the methods of the invention to provide sensitive and specific diagnostic tests for these and other diseases.

According to the invention, the methods are useful where a target epitope is accessible in either one of a non-wildtype protein (i.e. disease protein) or a wild type protein and inaccessible in the other. Inaccessibility is often due to aggregation making the target epitope inaccessible.

The invention includes a method of detecting whether a candidate polypeptide including a target epitope is a disease (disorder) polypeptide or a wild type polypeptide, comprising:

contacting the candidate polypeptide with a blocking agent; and determining whether the target epitope is inaccessible or accessible to chemical modification by the blocking agent.

The accessibility or inaccessibility of the target epitope is indicative of whether the candidate polypeptide is a disease (disorder) polypeptide or a wild type polypeptide because in one of the disease (disorder) protein and the wild type protein, the target epitope is accessible. In the other polypeptide the target epitope is inaccessible.

In one embodiment, the invention provides a method of detecting prion diseases, for example, determining whether a candidate polypeptide including a target epitope is in a wildtype conformation or in a non-wildtype conformation in which it is aggregated, comprising:

reacting a sample of polypeptide (the sample typically contains $PrP^{Sc}$ and/or $PrP^C$, and in many cases an abundance of one or the other) with a chemical modifying agent, typically an agent which chemically reacts with proteins such as peroxynitrite, which modifies accessible epitopes (target epitopes) so that they cannot bind to a detection agent;

disaggregating and/or denaturing the polypeptide in the sample; and probing with detection agents, such as an antibody against a target epitope, to determine whether the polypeptide (such as prior to disaggregation and/or denaturing) included inaccessible target epitopes.

$PrP^C$ is rendered "invisible" in the assay, because epitopes on the monomeric molecules are blocked to antibody recognition by the chemical modifying agent, whereas molecules of $PrP^{Sc}$ are "protected" from chemical modification by virtue of being sequestered within aggregates or otherwise unavailable for reacting. Alternatively, epitopes on the multimeric molecules are blocked to antibody recognition by the chemical modifying agent, whereas molecules of $PrP^{C}$ are "protected" from chemical modification by virtue of a difference in accessible epitopes.

In another embodiment, the Alzheimer's disease detection method comprises:

- reacting a sample of polypeptide (the sample typically contains all or part of diseased amyloid precursor polypeptide or A beta or tau and/or the corresponding wild type polypeptide, and in many cases an abundance of one or the other) with a chemical modifying agent, typically an agent which chemically reacts with proteins such as peroxynitrite, which modifies exposed epitopes so that they cannot bind to a detection agent;
- disaggregating and/or denaturing the polypeptide in the sample; and
- probing with detection agents, such as an antibody against a target epitope to determine whether the polypeptide prior to disaggregation and/or denaturing, included inaccessible target epitopes.

In further embodiments, the invention provides disease detection methods for other diseases characterized by differentially accessible target epitopes in disease and wildtype conformations, for example, resulting from misfolded and/or aggregated proteins such as Parkinson's disease (PD), Lewy Body disease (LBD), Huntington's disease (HD), amyotrophic lateral sclerosis (ALS), diabetes, and cancer. These methods similarly include steps such as reacting a sample of polypeptide (eg. a disease polypeptide described herein) with a chemical modifying agent, which modifies exposed epitopes so that they cannot bind to a detection agent; then disaggregating and/or denaturing the polypeptide in the sample; and probing with detection agents, such as an antibody against a target epitope to determine whether the polypeptide prior to disaggregation and/or denaturing, included inaccessible target epitopes. These steps are similarly adapted for other purposes, such as screening blood and blood products, and other uses described herein.

The method of the invention has many advantages over existing technology. As noted above, the invention is optionally referred to as "EPA", which in the case of prion protein disease detection is a simple, efficient method for detecting aggregated disease proteins such as $PrP^{Sc}$, the pathogenic molecule which is thought to constitute the infectious particle in prion diseases and polypeptide, associated with AD.

The invention is useful in high-throughput robotic-capable platforms. For example, EPA is not dependent on PrP protease resistance, the basis of most commercially available diagnostic tests for prion disease. Epitope protection technology does not require a protease digestion step, which makes it more sensitive to early infection. Certainly, the absence of a protease digestion step permits EPA to be more amenable to high-throughput robotic platforms.

In addition, the methods of the invention can be used to detect any protein that exists in two or more conformations, where one or more target epitopes are concealed in at least one conformation.

Accordingly, the invention relates to a detection method comprising:

- reacting a sample of polypeptide with a chemical modifying agent, typically an agent which chemically reacts with proteins, which is defined to modify exposed epitopes so that they cannot bind to detection agents;
- disaggregating and/or denaturing the polypeptide in the sample; and
- probing with detection agents, such as antibodies against a target epitope to determine whether the polypeptide prior to disaggregation and/or denaturing, included target epitopes inaccessible to the chemical modifying agent.

The result indicates whether the polypeptide includes inaccessible epitopes, which is indicative of the type of polypeptide that is present (i.e. wild type protein or non-wild type protein).

In one embodiment, the invention includes a method of detecting whether a candidate polypeptide including a target epitope is in a wildtype conformation or a non-wildtype conformation (in one embodiment, in the non-wildtype conformation, the candidate polypeptide aggregates with aggregated polypeptide), comprising:

- contacting the polypeptide with a blocking agent that selectively blocks accessible target epitopes, wherein in one of the non-wildtype conformation or the wildtype conformation, the target epitope is accessible and reacts with the blocking agent, and wherein in the other conformation, the target epitope is inaccessible and does not react with the blocking agent. Unreacted blocking agent is removed from contact with the polypeptide, for example, by allowing time for blocking agent to be consumed or degraded or by actively removing it by physical or chemical processes as described below;
- modifying the candidate polypeptide to convert any inaccessible target epitope to accessible target epitope; and
- contacting the polypeptide with a detection agent that binds selectively to target epitope that was converted from inaccessible target epitope to accessible target epitope, wherein binding between detection agent and converted target epitope indicates that prior to conversion the candidate polypeptide was in a conformation in which the target epitope was inaccessible and wherein lack of binding between the detection agent and the target epitope indicates that the polypeptide was in a conformation in which the target epitope was accessible, thereby indicating whether the polypeptide was in a wildtype conformation or a non-wildtype conformation.

The invention also includes a method of detecting whether a candidate polypeptide including a target epitope is in a wildtype conformation or a non-wildtype conformation, comprising:

- contacting the polypeptide with a blocking agent that selectively blocks accessible target epitope, wherein in the wildtype conformation, the target epitope is accessible and reacts with the blocking agent, and wherein in the non-wildtype conformation, the target epitope is inaccessible and does not react with the blocking agent. Unreacted blocking agent is removed from contact with the polypeptide, for example, by allowing time for blocking agent to be consumed or degraded or by actively removing it by physical or chemical processes as described below;
- modifying the candidate polypeptide to convert any inaccessible target epitope to accessible target epitope; and
- contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wildtype conformation.

The invention also includes a method of detecting whether a candidate polypeptide including a target epitope is in a wildtype conformation or a non-wildtype conformation, comprising:

contacting the polypeptide with a blocking agent that selectively blocks accessible target epitope, wherein in the non-wildtype conformation, the target epitope is accessible and reacts with the blocking agent, and wherein in the wildtype conformation, the target epitope is inaccessible and does not react with the blocking agent. Unreacted blocking agent is removed from contact with the polypeptide, for example, by allowing time for blocking agent to be consumed or degraded or by actively removing it by physical or chemical processes as described below;

modifying the candidate polypeptide to convert any inaccessible target epitope to accessible target epitope; and contacting the polypeptide with a detection agent that binds selectively to target epitope that was converted from inaccessible target epitope to accessible target epitope, wherein binding between detection agent and converted target epitope indicates that the candidate polypeptide was in a wildtype conformation and wherein lack of binding between the detection agent and the target epitope indicates that the polypeptide was in a non-wildtype conformation.

The invention also includes a method of detecting whether a candidate polypeptide including target epitope which has been reacted with a blocking agent, is in a wildtype conformation or a non-wildtype conformation, comprising:

modifying the candidate polypeptide to convert any inaccessible target epitope to accessible target epitope;

contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wild type conformation.

In the methods of the invention, the epitope is in many cases inaccessible in the misfolded or non-wild type conformation because i) the differential misfolding of the polypeptide compared to the wild type folded polypeptide prevents or reduces reaction between the blocking agent and the target epitope, ii) the polypeptide in the misfolded conformation aggregates with itself or other polypeptides in the misfolded conformation to prevent or reduce reaction between the protecting/blocking agent and the target epitope, and/or iii) post translational modifications of the polypeptide prevent or reduce reactions between the blocking agent and the target epitope.

In one example, the candidate polypeptide comprises prion protein, the wild type folded conformation comprises the conformation of wild type folded prion protein and the misfolded conformation comprises the conformation of $PrP^{Sc}$. Alternatively, the wild type folded protein comprises the conformation of APP or its cleavage product amyloid beta, and the misfolded conformation comprises the conformation of Alzheimer's disease APP or its cleavage product amyloid beta.

In another example, the candidate polypeptide comprises, SOD1, alpha-synuclein, islet amyloid polypeptide, resistin or p53 protein. The methods and kits of the invention described in the application are useful, for example, for application to a non-wildtype polypeptide having a conformation comprising multiple copies of a polypeptide aggregated together through interactions of beta-sheet-rich areas of the polypeptide. In one embodiment the polypeptide is polypeptide that is aggregated in prion protein aggregates. In another embodiment, the polypeptide is polypeptide that is aggregated in amyloid plaques.

The invention also includes i) polypeptide of the invention modified by reaction with a blocking agent listed herein and ii) the polypeptide modified by reaction with a detecting agent. The invention also includes compositions and kits of the invention including these modified polypeptide.

The blocking agent is optionally peroxynitrite, hydrogen peroxide, diethyl pyrocarbonate (DEPC), 4-hydroxynonenal (4HNE) an epoxide such as conduritol-B-epoxide and 1,2-epoxy-3-(p-nitrophenoxy)propane, methylene or diazirine and related compounds. In the methods, the polypeptide is optionally modified by denaturing the polypeptide, for example with heat, detergent and/or chaotropic agents. The polypeptide is optionally modified by treatment with a disaggregation agent to disaggregate the polypeptide from other polypeptides of the same type, and from other molecules, wherein the disaggregation agent is optionally selected from at least one of the group consisting of chaotropic agent (including guanidine salts, urea or thiourea), detergent and heat.

It is readily apparent to a skilled person that the method steps of the invention recited here involving removing the blocking agent typically involve physically, chemically or otherwise removing the blocking agent away from the candidate polypeptide to prevent further reaction. Removal optionally involves allowing a sufficient time to pass so that the blocking agent is removed from the candidate polypeptide by being consumed or degraded (for example, such that the blocking agent becomes inert or oxidized). Removal optionally involves adding a compound to react with any excess blocking agent to inactivate it. Removal also optionally involves physical filtering of the blocking agent by conventional filtration techniques or centrifugation to separate the candidate polypeptide and blocking agent, or physical binding to a substrate useful for removing the blocking agent, such as by binding of blocking agent or candidate polypeptide to an immobilized substrate in a column.

Removing means preventing further reactions by the blocking agent by, for example, physically or chemically inactivating the blocking agent, taking the blocking agent out of contact with the sample including the candidate polypeptide or allowing a sufficient amount of time to pass for the blocking agent to be consumed or degraded.

The detection agent optionally comprises an antibody directed against a prion polypeptide epitope, an amyloid beta epitope, an alpha-synuclein epitope or a SOD1 epitope. The antibody optionally comprises all or part of the anti-prion antibodies 6H4 and 3F4, and the anti-amyloid beta antibodies 6E10 and 4G8.

The methods of the invention are preferably used with mammals, such as humans. In addition, the methods of the invention are preferably used with mammals, such as livestock. In addition the methods of the invention are used with food items, cosmetic items, dental and surgical instruments vacuums and pharmaceutical products.

The invention also includes a method of testing a sample from an animal, using methods of the invention described herein, to determine if the animal has a disease characterized by the presence of candidate polypeptide in a non-wildtype conformation in the sample, wherein the candidate polypeptide includes a target epitope. Such diseases are described herein. In one embodiment, the method comprises; determining whether the candidate polypeptide is in i) a wildtype conformation or ii) a non-wildtype conformation, by a method comprising the steps of:

contacting the sample with a blocking agent that selectively blocks accessible target epitope in the candidate polypeptide, wherein in the wildtype conformation, the target epitope is accessible and reacts with the blocking agent, and wherein in the non-wildtype conformation, the target epitope is inaccessible because the candidate polypeptide is aggregated with the aggregated polypeptide and the target epitope cannot react with the blocking agent;

contacting the sample with a conversion agent to modify the candidate polypeptide to convert any inaccessible target epitope in the sample to accessible target epitope;

contacting the polypeptide with a detection agent that binds selectively to target epitope that was converted from inaccessible target epitope to accessible target epitope, wherein binding between detection agent and converted target epitope indicates that the candidate polypeptide was in a non-wildtype conformation and the animal has a disease and wherein lack of binding between the detection agent and the target epitope indicates that the polypeptide was in a wild type conformation.

The invention also includes a method of the invention described herein for screening, for example, by testing a sample, such as blood or blood products and other samples, to determine if the sample comprises a candidate polypeptide in a non-wildtype conformation wherein the candidate polypeptide includes a target epitope. In one embodiment, the method comprises; determining whether the candidate polypeptide is in i) a wildtype conformation or ii) a non-wildtype conformation, by a method comprising the steps of:

contacting the sample with a blocking agent that selectively blocks accessible target epitope in the candidate polypeptide, wherein in the wildtype conformation, the target epitope is accessible and reacts with the blocking agent, and wherein in the non-wildtype conformation, the target epitope is inaccessible and cannot react with the blocking agent;

contacting the sample with a conversion agent to modify the candidate polypeptide to convert any inaccessible target epitope in the sample to accessible target epitope;

contacting the polypeptide with a detection agent that binds selectively to target epitope that was converted from inaccessible target epitope to accessible target epitope, wherein binding between detection agent and converted target epitope indicates that the candidate polypeptide was in a non-wildtype conformation and the sample comprises a candidate polypeptide in a non-wildtype conformation and wherein lack of binding between the detection agent and the target epitope indicates that the polypeptide was in a wild type conformation.

In another embodiment, the invention relates to a method of detecting whether a candidate polypeptide including a target epitope is in i) a wildtype conformation or ii) a non-wildtype conformation (for example, wherein the polypeptide aggregates in the non-wildtype conformation), comprising:

contacting the polypeptide with a blocking agent that selectively blocks accessible target epitope, wherein in the wildtype conformation, the target epitope is accessible and reacts with the blocking agent, and wherein in the non-wildtype conformation, the target epitope is inaccessible (for example, because the candidate polypeptide is aggregated) and the target epitope cannot react with the blocking agent;

modifying the candidate polypeptide to convert inaccessible target epitope to accessible target epitope; and contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wild type conformation. One also removes unreacted blocking agent from contact with the polypeptide, for example, by allowing it to be consumed or degraded or removing it from the reaction by physical or chemical processes.

The candidate polypeptide optionally comprises prion protein, the wild type conformation comprises the conformation of wild type prion protein and the non-wildtype conformation comprises the conformation of $PrP^{Sc}$. The candidate polypeptide optionally comprises beta-amyloid polypeptide, tau protein or APP protein, SOD1, alpha-synuclein, huntingtin protein, p53 or islet amyloid polypeptide or resistin. The blocking agent is optionally selected from the group consisting of peroxynitrite, hydrogen peroxide, methylene compounds, succinic anhydride, epoxides, diethyl pyrocarbonate, 4-hydroxynonenal (4HNE) and diazirine. The polypeptide is optionally modified by denaturing the polypeptide. The polypeptide is also optionally denatured by heat and/or detergent and/or chaotropic agents. The polypeptide is optionally modified by treatment with a disaggregation agent to disaggregate the polypeptide from the aggregated polypeptides. The disaggregation agent is optionally selected from at least one of the group consisting of chaotropic agents, detergent and heat. The detergent optionally comprises SDS. The detection agent optionally comprises an aptamer or an antibody, for example, directed against a prion polypeptide epitope. The antibody optionally comprises 6H4 or 3F4. The aptamer or antibody is optionally directed against an amyloid beta epitope. The antibody optionally comprises 6E10 or 4G8. The non-wildtype conformation is in certain embodiments indicative of a disease caused by protein aggregation, such as prion disease (eg. BSE or CJD), Alzheimer's disease, Parkinson's disease or Lewy body disease, Huntington's disease, amyotrophic lateral sclerosis, cancer or diabetes. Optionally, prior to contacting the blocking agent with the candidate polypeptide, the candidate polypeptide is in a sample that is pretreated by one or more of the following methods: adsorption, precipitation, or centrifugation. Optionally, prior to contacting the blocking agent with the candidate polypeptide, the target epitope is mapped (ie., the epitope is identified, for example, as described below under the "Target Epitopes" section). Optionally, the polypeptide is in a postmortem or antemortem sample selected from the group of: CSF, serum, blood, urine, biopsy sample or brain tissue. Another aspect of the invention relates to a kit for detecting whether a candidate polypeptide including a target epitope is in i) a wildtype conformation or ii) a non-wildtype conformation, comprising a detecting agent that recognizes the target epitope and instructions for at least one of i) mapping a target epitope, ii) contacting a candidate polypeptide with a blocking agent, and iii) contacting a candidate polypeptide with a detecting agent. The kit is useful to implement method of the invention described herein. The detecting agent optionally comprises an aptamer or an antibody. The antibody optionally comprises 6H4, 3F4, 6E10 or 4G8, optionally immobilized to a solid support. The kit optionally further comprises buffers and reagents, for example, for ELISA, such as sandwich ELISA, fluorescent ELISA. The kit optionally further comprises a blocking agent. The kit optionally further comprises a denaturing agent selected from at least one of the group of detergents and chaotropic agents. The kit optionally further comprises a polypeptide standard. The kit optionally comprises a recombinant disease protein or a recombinant protein that mimics a disease protein. In another embodiment, the invention relates to method of detecting whether a candidate polypeptide that has been contacted with a blocking agent is i) a wildtype conformation or ii) a non-wildtype conformation, wherein the candidate polypeptide comprises at least one target epitope and, following contact with the blocking agent and removal of the blocking agent, the candidate polypeptide has been modified to convert any inaccessible target epitope to accessible target epitope, the method comprising: contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation (for example, an aggregated conformation) and wherein lack of binding between the detection agent and the target epitope indicates that the polypeptide was in a wild type conformation. Diseases, blocking agents, target epitopes, detecting agents and other aspects described herein are also useful in this method. The diseases, blocking agents, target epitopes, detecting agents and other aspects described herein are also readily adapted for the methods described in preceding paragraphs, such as methods for testing a sample from an animal (such as a human, livestock etc.) to determine if the animal has a disease or screening a sample.

The reverse situation to the methods described in some of the aforementioned paragraphs is also usefully detected, for example, where the wildtype conformation includes an inaccessible epitope and the non-wild type conformation has an accessible epitope. This situation is also readily adapted to methods described herein, such as diagnosing disease or screening samples.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Embodiments of the invention are described in relation to the drawings in which.

The 6E10 epitope in the Abeta region of APP is less accessible to peroxynitrite modification in Alzheimer's disease brain compared to normal brain (panel A), and in brain homogenates that have been treated at low pH to induce protein aggregation (panel B). Abeta 1-42 peptide aggregated in vitro shows prominent epitope protection of the 6E10 epitope to peroxynitrite modification, in comparison with soluble non-aggregated Abeta 1-42 (panel C). Normal and aggregated Abeta 1-42 treated with increasing concentrations of peroxynitrite and them immunoblotted with 6E10 antibody also shows prominent epitope protection (panel D).

Figure 5:
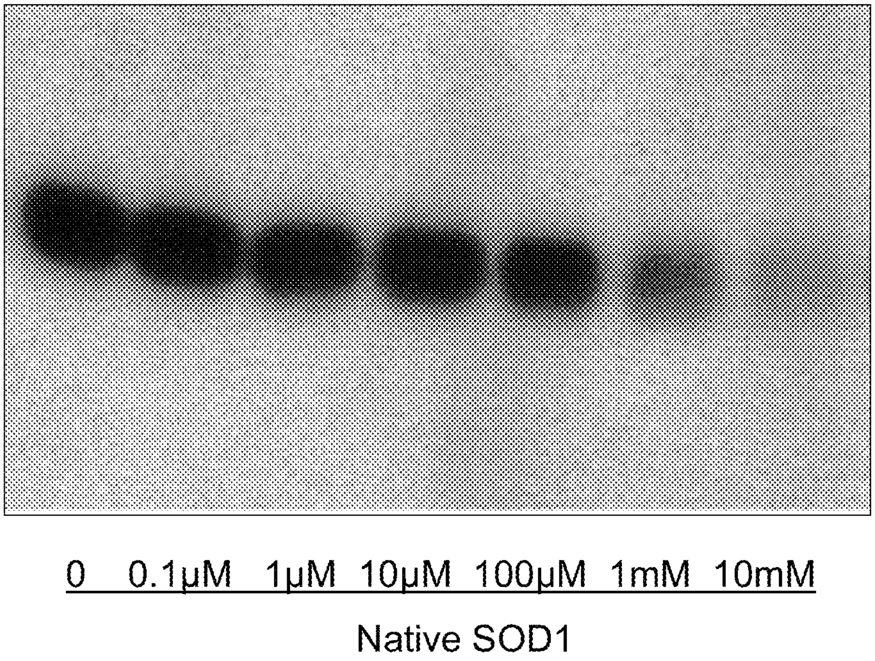
Figure 5:
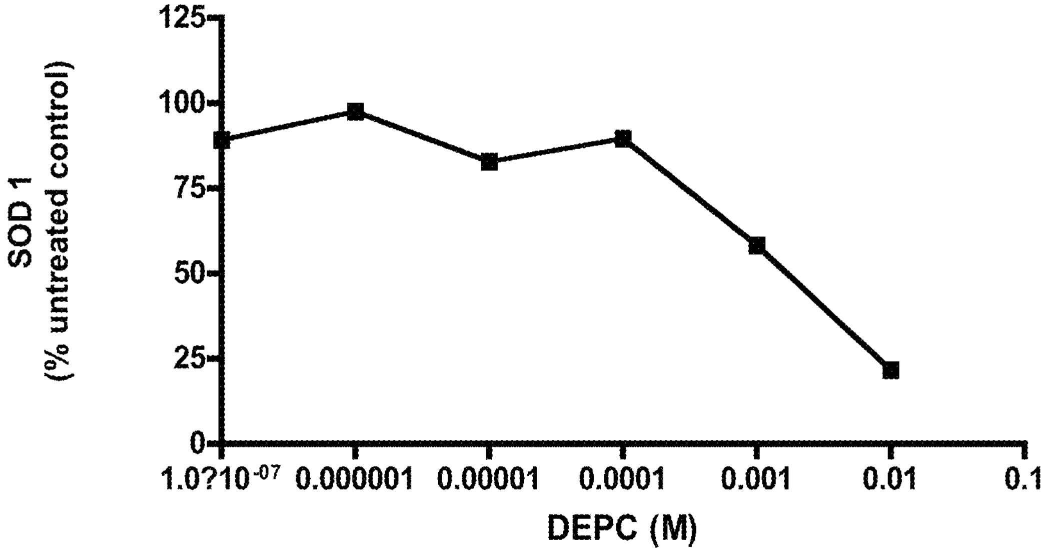

FIG. 5 Detection of Epitopes Modifiable by DEPC in SOD1

(A) Western blot showing soluble SOD1 treated with increasing concentrations of DEPC and immunoblotted with sheep anti-SOD1. (B) Graphical representation of decreasing antibody binding to SOD1 with increasing DEPC-concentration.

Figure 6:
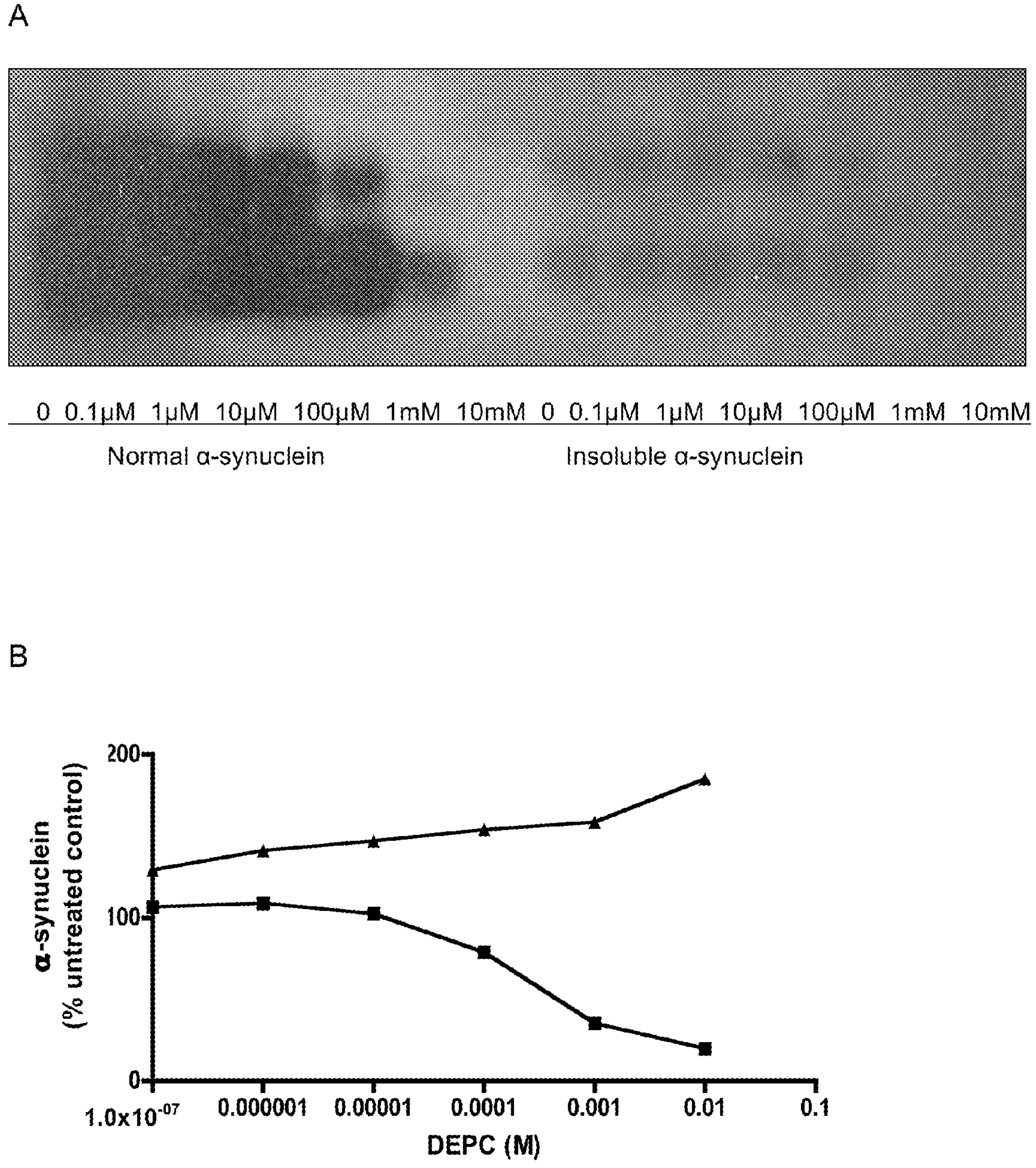

FIG. 6 Detection of Aggregated Alpha-Synuclein Using EPA (A) Western blot showing effect of increasing concentrations of DEPC on antibody binding to soluble and insoluble alpha-synuclein. (B) Graphical representation showing the extent of antibody binding to normal (■) and insoluble (▲) alpha-synuclein.

DETAILED DESCRIPTION OF THE INVENTION

The current invention provides a useful method for the detection of a disease related polypeptide counterpart of a normal cellular polypeptide which forms aggregates or otherwise leads to the obscuration of one or more epitopes that are not obscured in the normal or wild type polypeptide. The invention recognizes the importance of aggregation in the pathology of diseases such as prion disease. The invention also takes advantage of this aggregation effect and provides an assay that overcomes problems with prior art detection assays. In one embodiment, the method of the invention is applied to the detection of $PrP^{Sc}$ in plasma, serum, urine or other biological sample. The methods of the invention are further useful for detecting any polypeptide that exists in two or more conformations, where one or more target epitopes are inaccessible in at least one conformation. In one embodiment the invention includes a method of detecting whether a candidate polypeptide including a target epitope is in a wild type or non-wild type conformation.

"Epitope" refers to a portion of a sequence of contiguous or non-contiguous amino acids (antigen) which is recognized by and bound by a detection agent such as an antibody. Preferably, the epitope is a linear epitope on a polypeptide which typically includes 3 to 10 or 6 to 10 or more contiguous amino acids that are recognized and bound by a detection agent. A conformational epitope includes non-contiguous amino acids. Sometimes conformational epitopes can re-establish themselves after denaturation by partial refolding on, e.g, an immunoblot membrane. The detection agent such as an antibody recognizes the 3-dimensional structure. When a protein molecule is folded into a three dimensional structure the amino acids forming the epitope are positioned in a manner that permits the detection agent to recognize and bind to the amino acids. In an unfolded (denatured) protein only the linear epitope is recognized and bound by the detection agent. Since the protein is unfolded prior to contact with the detection agent, the inaccessible epitope will typically be a linear epitope.

"Blocking agent" refers to an agent that reduces epitope reactivity, for example by binding to the epitope or by modifying and destroying epitope reactivity, for example on an amino acid side group within a linear epitope, so that the epitope is prevented from binding to detection agent (usually but not always an antibody). An example of a blocking agent is peroxynitrite. Other examples would include methylene, hydrogen peroxide, diethyl pyrocarbonate, 4-hydroxynonenal (4HNE) epoxides such as conduritol-B-epoxide and 1,2-epoxy-3-(p-nitrophenoxy)propane and diazirine. Chemical modifying agents that saturate accessible amino acids critical for epitope recognition in native conditions are most useful in the applications of epitope protection technology. Additionally the blocking agent may phosphorylate, glycosylate or otherwise modify a target-epitope. The blocking agent may also include peptides, antibodies or antibody fragments that bind to the epitope. The blocking agent should efficiently modify accessible amino acids (e.g. modify at least: 50%, 75%, 90%, 95% or 99% of accessible amino acids).

"Accessible epitope" is target epitope that is available to react with blocking agent in methods of the invention. For example, epitope that is available to react with blocking agent is accessible epitope. After reacting with blocking agent, the accessible epitope is prevented from binding to detection agent (after this reacting step, the reacted epitope may be referred to as the blocked epitope).

"Antibody" is intended to include whole antibodies and fragments thereof which also specifically react with one or more protein epitopes, such as disease protein epitopes. Antibodies can be fragmented using conventional techniques and the fragments screened for utility in the same manner as described below. For example, F(ab')2 fragments can be generated by treating antibody with pepsin. The resulting F(ab')2 fragment can be treated to reduce disulfide bridges to produce Fab' fragments.

"Aptamer" means a macromolecule such as a peptide, RNA or DNA molecule that is able to specifically interact with a protein or peptide target.

"Inaccessible epitope" means that target epitope modification by the chemical blocking agent is prevented or significantly reduced (e.g. reduced by at least: 50%, 75%, 90%, or 95%), for example, by differential misfolding relative to the wild type polypeptide, by aggregation of misfolded polypeptide or by post-translational modifications of the polypeptide. In some cases, inaccessible epitope is converted to accessible epitope by removing the hindrance (e.g. misfolding or aggregation) that prevents or significantly reduces target epitope modification by the blocking agent. The inaccessible epitope that is converted to accessible epitope may also be called "revealed epitope".

"Detection agent" refers to an agent that binds to epitope and which may be detected, such as antibody specific for prion polypeptide epitopes that can be used to probe the sample containing the polypeptide. The detection agent is used after the polypeptide is unfolded such that the detection preferentially binds the unblocked, unmodified epitopes.

"Disease protein or disease polypeptide" refers to a polypeptide associated with a disease or disorder state where the modular or higher order conformation of the polypeptide differs from the wild type or non-disease conformation and includes mutants, variants and polymorphic versions thereof. A disease protein or disease polypeptide can also be referred to as non-wild type conformation protein or polypeptide. The modular conformation refers to conformational changes in the three dimensional structure of a single protein molecule. The higher order conformation refers to conformational changes in the three dimensional structure of many protein molecules aggregated together. The aggregation can consist of one or more different proteins and can be associated with non-protein molecules. The wildtype and non-wildtype candidate polypeptides including disease proteins or polypeptides also include recombinant proteins, such as cellularly expressed (i.e. bacteria, using baculovirus systems etc.) and in vitro translated polypeptides "Wildtype folded conformation" refers to the wild type, folded conformation of protein in a non-disease or non-disorder state.

"Misfolded conformation" refers to the folded conformation of polypeptide in a disease or disorder state where the conformation differs from the wild type conformation. The difference in conformation is as a result of differential folding. The differential folding may cause protein aggregation.

"Wildtype conformation" refers to the conformation of polypeptide in its usual or normal state or in a reference or desired state and can include polypeptide in a non-disease or disorder state.

"Non-wildtype conformation" refers to a conformation of polypeptide that differs from the conformation of the wild type polypeptide and can include a conformation of polypeptide in a disease or disorder, where the conformation differs from the wild type conformation. The difference in conformation may be as a result of differential folding, polypeptide aggregation or differential post-translational modification compared to the wild type polypeptide. In the case of polypeptide aggregation, the aggregation may prevent accessibility of the epitope rather than the changed conformation.

Neurodegenerative diseases, such as Alzheimer's disease (AD), amyotrophic lateral sclerosis (ALS) and Parkinson's disease/Lewy body dementia (PD, LBD) pose major challenges to the aging population and health care system. No specific biochemical test exists for neurodegenerative diseases as a group (1,2). Sporadic AD, ALS, and PD/LBD are all associated with neural accumulation of pathological multimers of misfolded polypeptides (such as fibrils, protofilaments, and amorphous aggregates), including the Abeta fragment of the amyloid precursor protein (APP) in AD; superoxide dismutase-1 (SOD1) in ALS, and alpha-synuclein in PD and LBD (1). As with prion diseases, mutations in genes encoding these aggregation-prone polypeptides are associated with autosomal dominant familial forms of AD, ALS, and PD. The detection of disease-associated misfolded polypeptide aggregates enables specific and sensitive antemortem diagnostic tests for neurodegenerative diseases.

To this end the inventors have invented the "epitope protection assay" (EPA), an innovative technology for detection of aggregated polypeptides in tissues and accessible biological fluids, such as blood and CSF, which serve as "sinks" for the aggregates released from dying neurons. The method optionally consists of:

- reacting a sample with a chemical modifying agent;
- disaggregating and denaturing the treated polypeptides;
- probing the sample with detection agents such as antibodies against specific epitopes blocked by the chemical modifier; and
- detection of agent-bound polypeptides (e.g., by ELISA).

Normal soluble polypeptides in the sample are rendered "invisible" in the assay, because accessible epitopes are not detected by a detecting agent (eg. blocked to antibody recognition), whereas a proportion of polypeptides in aggregates are "protected" from chemical modification by virtue of their interior sequestration, and are still available to be detected by a detecting agent (eg. bind antibody) after disaggregation.

The methods of the invention are useful to diagnose diseases characterized by polypeptide misfolding and/or aggregation such as in the diseases mentioned above or for diseases or disorders characterized by polypeptides with otherwise differentially accessible target epitopes in disease and wildtype protein conformations.

The present inventors have also found that treatment of recombinant mouse prion polypeptide (rmPrP) at low pH in the presence of low concentrations of denaturants causes the polypeptide to acquire increased beta-sheet content, reminiscent of the misfolded disease-associated prion polypeptide isoform, $PrP^{Sc}$. This conversion of rmPrP is associated with increased solvent accessibility of tyrosine side chains[4]. The inventors have found that treatment of normal brain homogenate with acid and denaturants causes PrP to become detergent insoluble (29). In order to probe the surface accessibility of tyrosines and other residues in normal and misfolded $PrP^{C}$, normal and acid-misfolded human brain tissue was treated with the chemical nitrating compound peroxynitrite. Peroxynitrite treatment of brain tissue caused a reduction in the binding of the anti-PrP antibodies 3F4 and 6H4 as measured by immunoblotting, immunoprecipitation and ELISA. Peroxynitrite-induced epitope blocking was more pronounced on normal brain PrP than on misfolded PrP, showing a protective effect of aggregation. Similar findings were observed in normal and scrapie-infected hamster brain, in which 3F4 and 6H4 epitopes of scrapie brain PrP were partially protected from peroxynitrite-induced modification. Immunoprecipitation of peroxynitrite-treated brain with anti-nitrotyrosine antibodies suggests that either PrP is nitrated on tyrosine residues or another polypeptide in proximity to PrP is nitrated and coimmunoprecipitates PrP.

Accordingly, the invention includes a method of determining polypeptide aggregation, including but not limited to $PrP^{Sc}$, comprising:

- reacting a sample with a chemical modifying agent where such agent could be, but is not limited to, peroxynitrite
- disaggregating and/or denaturing the chemically modified sample with heat, detergent, or chaotropic agents; and
- probing with antibodies specific for prion polypeptide epitopes.

The inventors have further shown that the methods of the invention are useful for detecting Alzheimer disease proteins.

In one embodiment, the Alzheimer's disease detection method comprises:

- reacting a sample of polypeptide (the sample typically contains all or part of a disease protein or polypeptide such as amyloid precursor polypeptide or amyloid beta or tau and/or the corresponding wild type polypeptide, and in many cases an abundance of one or the other) with a chemical modifying agent, typically a blocking agent such as peroxynitrite, which modifies exposed epitopes so that they cannot bind to a detection agent;
- disaggregating and/or denaturing the polypeptide in the sample; and
- probing with detection agents, such as an antibody against a target epitope to determine whether the polypeptide prior to disaggregation and/or denaturing, included inaccessible target epitopes.

Abeta containing vascular or plaque filaments are also associated with conditions such as trisomy 21 (Down's syndrome), hereditary cerebral hemorrhage with amyloidosis (HCHWA)-Dutch type, and normal brain aging (Mori, H et al. JBC (1992) 267: 17082-86). Accordingly, in one embodiment detection of Abeta disease protein is prognostic for diseases HCHWA-Dutch type or normal brain aging.

In addition, the methods of the invention can be combined with other diagnostic methods such as magnetic resonance imaging (MRI) or computed tomography (CT) scans to confirm diagnosis.

The methods of the invention are useful to detect protein or polypeptide including target that exists in two or more conformations, where one or more target epitopes are concealed in at least one conformation.

Accordingly, the invention relates to a detection method comprising:

- reacting polypeptide with a chemical modifying agent, typically a blocking agent, which is defined to modify exposed epitopes so that they cannot bind to detection agents;
- disaggregating and/or denaturing the polypeptide in the sample; and
- probing with detection agents, such as antibodies against target epitope to determine whether the polypeptide prior to disaggregation and/or denaturing, included target epitopes inaccessible to the chemical modifying agent.

The result indicates whether the polypeptide includes inaccessible epitopes, which is indicative of the type of polypeptide that is present (i.e. wild type or non-wild type protein).

The invention also includes a method of detecting whether a candidate polypeptide including a target epitope that has been reacted with a blocking agent, is in a wildtype conformation or a non-wildtype conformation, comprising:

modifying the candidate polypeptide to convert any inaccessible target epitope to accessible target epitope; and contacting the polypeptide with a detection agent that binds selectively to the target epitope that was converted from inaccessible target epitope to accessible target epitope, wherein binding between detection agent and converted target epitope indicates that the candidate polypeptide was in a non-wildtype conformation and wherein lack of binding between the detection agent and the target epitope indicates that the polypeptide was in a wild type conformation.

In another application, the invention also includes a method of detecting intrinsically modified polypeptide, wherein the modification protects target epitope from reacting with the detecting agent, comprising:

contacting the polypeptide with a blocking agent that selectively blocks accessible target epitope, wherein in one of the non-wildtype conformation or the wildtype conformation, the target epitope is accessible and reacts with the blocking agent, and wherein in the other conformation, the target epitope is inaccessible and does not react with the blocking agent;

reacting the sample with an agent that removes the intrinsic modification from the intrinsically modified polypeptide target epitope;

disaggregating and/or denaturing the polypeptide in the sample; and probing with a detection agent, such as antibodies against the target epitope, to determine whether the candidate polypeptide is an intrinsically modified polypeptide.

Chemical Modifying Agents

The chemical modifying agent of the invention comprises any chemical (including a biological agent) that modifies target epitope residues such that the epitope is rendered invisible by the methods of the invention (ie. not detected by the detecting agent or detection is reduced). For example, peroxynitrite preferentially modifies tyrosine, serine, methionine, histidine and tryptophan as well as cysteine and other amino acids (25, 26). DEPC preferentially modifies histidines (37), and succinic anhydride preferentially modifies residues comprising amines. Epoxides, including conduritol-B-epoxide and 1,2-epoxy-3-(p-nitrophenoxy) propane) are a reactive group used widely for "suicide inhibition" of carboxyl group side chains, such as the catalytic residues of aspartyl proteases (19, 20). Hydrogen peroxide and methylene are also useful. The chemicals may modify the target epitope by oxidizing, nitrating, reducing, or otherwise modifying the epitope. In addition, the epitope may be modified by a chemical modifying agent that is a phosphate group (by phosphorylation), or a gylcosyl group (by gylcosylation), and/or other chemical group that obscures the target epitope.

Accordingly, in one embodiment the chemical modifying agent is chosen from the group peroxynitrite, DEPC, hydrogen peroxide, succinic anhydride, methylene and epoxides (conduritol-B-epoxide and 1,2-epoxy-3-)p-nitrophenoxy) propane and/or related variants thereof.

After reacting with candidate polypeptides, the chemical modifying agent is removed. It is readily apparent to a skilled person that the method steps of the invention recited here involving removing the blocking agent typically involve physically, chemically or otherwise removing the blocking agent away from the candidate polypeptide to prevent further reaction. Removal optionally involves allowing a sufficient time to pass so that the blocking agent is removed from the candidate polypeptide by being consumed or degraded (for example, such that the blocking agent becomes inert or oxidized). Removal optionally involves adding a compound to react with any excess blocking agent to inactivate it. Removal also optionally involves physical filtering of the blocking agent by conventional filtration techniques or centrifugation to separate the candidate polypeptide and blocking agent, or physical binding to a substrate useful for removing the blocking agent, such as by binding of blocking agent or candidate polypeptide to an immobilized substrate in a column.

Removing means preventing further reactions by the blocking agent by, for example, physically or chemically inactivating the blocking agent, taking the blocking agent out of contact with the sample including the candidate polypeptide or allowing a sufficient amount of time to pass for the blocking agent to be consumed or degraded.

Chemical modification of a target epitope leads to obscuration of an epitope to antibody recognition. In one embodiment treatment with a blocking agent such as peroxynitrite leads to destruction of epitopes on monomeric proteins but not epitopes on aggregated proteins such as non-wild type polypeptides or disease proteins.

Pretreatment

The methods of the invention also contemplate pretreatment of the sample to enhance EPA detection. For example if decreased detection of aggregated proteins such as prions in blood or urine is observed, pre-clearing strategies are readily employed to enhance detection with detergents, precipitating agents, and adsorbents such as those typically used in commercial ELISA assays which are known to one skilled in the art. Polypeptide samples may also be pretreated with agents such as detergents or guanidine or heat. Finally samples may be concentrated or precleared by methods such as centrifugation. Accordingly, in one embodiment the samples are pretreated before employing a method of the invention.

Detecting Misfolded or Aggregated Proteins and Polypeptides

The inventors have found a method that detects polypeptides that have target epitopes that are accessible to detection in one conformation and inaccessible in another by modification of inaccessible epitopes by a modifying agent. The inventors have identified several epitopes that are useful as target epitopes in the methods of the invention. Other target epitopes are identified as described below.

Target Epitopes

Target epitopes are identified for polypeptides that exist in two or more conformations wherein epitopes that can be detected by detecting agents such as antibodies, aptamers or peptides, are accessible in one conformation and inaccessible in the other conformation. Where an epitope is found to be blocked from detection by a blocking agent in one conformation of the polypeptide, the epitope is a target epitope. To identify target epitopes, a detection agent such as an antibody is chosen. If the detection agent is an antibody it is preferably a monoclonal antibody although polyclonal antibodies are also usable. The epitope, which can be a linear or non-linear epitope, and which is specifically recognized by the antibody, is optionally a known epitope. A candidate chemical modifying agent such as peroxynitrate is chosen. If the epitope recognized by the detection agent is known, the candidate chemical modifying agent is preferably chosen based on its ability to modify amino acid residues in the target epitope. For example peroxynitrite preferentially modifies tyrosine and histidine residues with some modification of cysteine and other amino acids. Peroxynitrite is optionally chosen as chemical modifying agent if tyrosines and/or histidines are present in the target epitope. Aliquots of a sample comprising wild type polypeptide and aliquots of a sample comprising non-wildtype polypeptide are reacted with increasing concentrations of the chosen chemical modifying agent. Each sample comprises one or more of recombinant polypeptide, cell extracts or tissue samples known to express the polypeptide in either the wild type or non-wild type conformation. Preferably samples of polypeptide have similar concentrations of polypeptide. The non-wildtype conformation polypeptide sample is alternatively obtained by treating a polypeptide in wild type conformation with an agent, such as acid, that induces conversion to a non-wildtype conformation.

Each sample of polypeptide is denatured and/or disaggregated to convert any inaccessible putative target epitope to accessible target epitope. Each sample of polypeptide is then contacted with the chosen detection agent. Detection is performed using techniques known in the art such as ELISA, and Western blotting. The amount of signal generated by the detection agent for sample comprising polypeptide in a wildtype conformation treated with protection agent and for sample comprising polypeptide in a non-wildtype conformation treated with protection agent are compared. A difference in detection at one or more concentrations of chemical modifying agent indicates that the epitope is protected in one conformation and further indicates that the epitope is a target epitope. A difference over a range of chemical modifying agent concentrations indicates that the target epitope is useful for EPA. The process is repeated with different blocking agents and/or detecting agents and target epitopes are identified. One typically standardizes and titrates the blocking agent and to performs experiments using a "universal" chemical modifier such as methylene[24,25], which optionally yields more uniform and complete protection of the target epitope.

Accordingly in one example, a method of identifying a target epitope in a polypeptide that has two or more conformations wherein the target epitope is accessible to detection in one conformation and inaccessible in another conformation comprises:

- reacting a sample comprising polypeptide in a wild type conformation and a sample comprising polypeptide in a non-wild type conformation typically with one or more concentrations of a chemical modifying agent;
- denaturing and/or disaggregating each sample to convert any inaccessible target epitope to accessible target epitope;
- contacting the samples with a detection agent; and
- comparing the signal generated by the detection agent for samples comprising polypeptide in a wildtype conformation treated with chemical modifying agent and for samples comprising polypeptide in a non-wildtype conformation treated with chemical modifying agent wherein a difference in detection between sample comprising wildtype polypeptide and sample comprising non-wild type sample indicates that the epitope is protected in one conformation and further indicates that the epitope is a target epitope.

Conditions for EPA

Titration experiments with peroxynitrite, hydrogen peroxide and methylene (based on UV light photolysis of the precursor diazirine) or other modifying agents, are useful to improve conditions for epitope protection.

Samples known to contain polypeptides in two or more conformations, including disease proteins, are optionally reacted using immunoblotting and ELISA. In each case, samples are prepared and optionally mixed with increasing concentrations of the modifying agent and processed, for example, by immunoblotting, ELISA and/or time resolved fluorescence. This defines the type and concentration of chemical agent allowing the maximal distinction between monomeric and aggregated proteins including disease proteins. Additional informative experiments can involve using recombinant disease (non-wild type) protein (such as acid treated prion proteins or mutant p53 proteins and other protein listed in this application) and normal (wild type) protein in place of samples containing disease proteins.

In some cases, disease proteins may have different properties for chemical modification than do recombinant disease proteins, and disease proteins in one sample type (such as brain tissue) may display different chemical modification properties than disease proteins circulating in blood, or detectable in urine. One of skill in the art shall readily identify the optimal conditions for endogenous prions using known techniques.

The EPA achieves superior commercial utility by detecting disease proteins in biological tissues and fluids for which no present technology exists. Some disease proteins are in very low abundance. For example prions are in very low abundance (10-100 prions/mL by bioassay), and protease-resistant PrP in urine is only intermittently/sporadically detectable by precipitation of large fluid volumes. Also, any prospective blood test must contend with high concentrations of wildtype protein (i.e. for $PrP^C$ (typically $10^6$-fold more than $PrP^{Sc}$)) and "blocking" by heterologous plasma proteins. Using the optimized chemical modification regimen and the DELFIA-TRF system, the sensitivity thresholds for EPA in blood and urine are optionally determined using:

1. Animal and human plasma and urine "spiked" with a titration of disease protein;
2. Plasma and urine from model disease animals expressing a disease protein.

Biological fluids clinically accessible by non-invasive routes provide a substrate for a practical antemortem test for diagnosis and screening of diseases involving aggregated disease proteins in humans and animals. The methods of this invention are also useful in post-mortem testing. One of skill in the art readily determines whether EPA with "disease protein spike" titration in normal blood and urine reveals similar DELFIA-TRF signals to the same disease protein titration in buffer, showing that the EPA is not affected by "blocking factors" in these biological fluids. Preferential "blocking" of disease protein by heterologous proteins may actually enhance epitope protection to chemical modifying agents. If decreased detection of disease protein in blood or urine is observed, pre-clearing strategies are readily employed to enhance disease protein detection, for example, with detergents, precipitating agents, and adsorbents typically used in commercial ELISA assays which are known to one skilled in the art.

In one embodiment, the methods of the invention involve the detection of target epitopes in misfolded or aggregated polypeptides. In another embodiment, the invention provides a method for improving or optimizing the detection of polypeptides that can exist in 2 or more conformations. In another embodiment the detection of misfolded and/or aggregated polypeptides is indicative of disease (disease proteins). In another embodiment, polypeptides are detected using detection agents such as antibodies, aptamers or peptides that specifically bind to epitopes of polypeptides that can be chemically modified. In another embodiment these polypeptides are disease proteins. Antibodies to candidate protein epitopes are commercially available antibodies or are readily prepared by a person skilled in the art and include antibody fragments, and single chain antibodies. All the aforementioned methods are readily implemented using steps described in this application.

Antibodies

The invention contemplates the use of known antibodies as the binding agent including biotin-3F4 and 3F4 and 6H4 which recognize prion disease proteins. 3F4 reacts against the MKHM (SEQ ID NO:1) epitope and 6H4 reacts against the DYEDRYYRE (SEQ ID NO:2) epitope. Additionally, 6E10 which recognizes Abeta, reacts against the EFRHDS (SEQ ID NO:3) epitope (residues 3-8).

Other antibodies and the epitopes recognized (if known) which are optionally used with the methods of the invention are listed in the table below.

TABLE

Antibodies useful to detect disease proteins

| Protein | Antibody | Mono/Poly | Epitope | Company |
|---|---|---|---|---|
| Abeta | 4G8 | Monoclonal | Within aa18-22 of human Abeta | Signet |
| | 6E10 | Monoclonal | Within aa3-8 of human Abeta | Signet |
| | ab2539 | Polyclonal | NA | Abcam |
| | Abeta-NT | Polyclonal | NA | QED Bioscience |
| | DE2B4 | Monoclonal | Within aa1-17 of human Abeta | Acris antibodies |
| | NBA-104E | Monoclonal | Within aa1-16 of human Abeta | Stressgen |
| Alpha-synuclein | 4D6 | Monoclonal | Unknown | Acris antibodies |
| | ab6162 | Polyclonal | NA | Abcam |
| | LB509 | Monoclonal | Unknown | Zymed |
| | Syn-1 | Monoclonal | Within aa91-99 of human a-syn | BD Biosciences |
| | Syn-204 | Monoclonal | Within aa87-110 of human a-syn | Lab Vision |
| | Syn-211 | Monoclonal | Within aa121-125 of human a-syn | Lab Vision |
| Tau | Mouse Anti-Tau-1 | Monoclonal | Within aa95-108 of human tau | Biomeda |
| | Mouse Anti-Tau-2 | Monoclonal | Unknown | Stressgen |
| | T14 | Monoclonal | Within aa141-178 of human tau | Zymed |
| | T46 | Monoclonal | Within aa404-441 of human tau | Zymed |
| | Tau-2 | Monoclonal | Unknown | Acris antibodies |
| | Tau-5 (ab3931) | Monoclonal | Unknown | Abcam |
| SOD1 | Mouse SOD1 | Monoclonal | Unknown | Sigma-aldrich |
| | Rabbit SOD1 | Polyclonal | Unknown | Stressgen |
| | Rat SOD1 | Polyclonal | Unknown | Stressgen |
| | Sheep SOD1 | Polyclonal | Unknown | OxisResearch |

Antibodies to disease protein epitopes are prepared using techniques known in the art. For example, by using a peptide of a disease protein including a putative target epitope, polyclonal antisera or monoclonal antibodies are made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide is administered in the presence of adjuvant. The progress of immunization can be monitored by detection of antibody titers in plasma or serum. Standard ELISA or other immunoassay procedures are optionally used with the immunogen as antigen to assess the levels of antibodies. Following immunization, antisera can be obtained and, if desired, polyclonal antibodies isolated from the sera.

To produce monoclonal antibodies, antibody producing cells (lymphocytes) are optionally harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated.

Chimeric antibody derivatives, i.e., antibody molecules that combine a non-human animal variable region and a human constant region are also contemplated within the scope of the invention. Chimeric antibody molecules include, for example, the antigen binding domain from an antibody of a mouse, rat, or other species, with human constant regions. Conventional methods used to make chimeric antibodies containing the immunoglobulin variable region which recognizes disease protein epitopes of the invention (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Specific antibodies, or antibody fragments, such as, but not limited to, single-chain Fv monoclonal antibodies reactive against disease protein epitopes are readily generated by screening expression libraries encoding immunoglobulin genes, or portions thereof, expressed in bacteria with peptides produced from the nucleic acid molecules of disease proteins. For example, complete Fab fragments, VH regions and FV regions are expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, is used to produce antibodies or fragments thereof.

Antibodies specifically reactive with disease protein epitopes, or derivatives, such as enzyme conjugates or labeled derivatives, are useful to detect disease protein epitopes in various samples (e.g. biological materials). They are useful as diagnostic or prognostic reagents and are readily used to detect abnormalities in the level of protein expression, or abnormalities in the structure, and/or temporal, tissue, cellular, or subcellular location of disease protein epitopes. In vitro immunoassays are also useful to assess or monitor the efficacy of particular therapies. The antibodies of the invention may also be used in vitro to determine the level of expression of a gene of a polypeptide that exists in two or more conformations such as a disease protein in cells genetically engineered to produce the disease protein.

The antibodies are useful in any known immunoassays which rely on the binding interaction between an antigenic determinant of the disease protein epitopes and the antibodies. Examples of such assays are radioimmunoassays, enzyme immunoassays (e.g. ELISA including Sandwich ELISA), immunofluorescence, immunoprecipitation, latex agglutination, hemagglutination, and histochemical tests. The antibodies are useful to detect and quantify the disease protein in a sample in order to determine its role and to diagnose the disease caused by the disease protein.

In particular, the antibodies of the invention are useful in immunohistochemical analyses, for example, at the cellular and subcellular level, to detect a disease protein, to localize it to particular cells and tissues, and to specific subcellular locations, and to quantitate the level of expression.

Cytochemical techniques known in the art for localizing antigens using light and electron microscopy to detect polypeptides such as disease proteins. Generally, an antibody of the invention is optionally labeled with a detectable substance and the recognized polypeptide is localised in tissues and cells based upon the presence of the detectable substance. Examples of detectable substances include, but are not limited to, the following: radioisotopes (e.g., $^{3}H$, $^{14}C$, $^{35}S$, $^{125}I$, $^{131}I$), fluorescent labels (e.g., FITC, rhodamine, lanthanide phosphors), luminescent labels such as luminol; enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or colorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualized by electron microscopy.

The antibody or sample may be immobilized on a carrier or solid support which is capable of immobilizing cells, antibodies etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against disease protein epitopes. By way of example, if the antibody having specificity against a polypeptide epitope such as a disease protein epitope is a rabbit IgG antibody, the second antibody may be goat anti-rabbit gamma-globulin labeled with a detectable substance as described herein.

Where a radioactive label is used as a detectable substance, disease proteins may be localized by autoradiography. The results of autoradiography may be quantitated by determining the density of particles in the autoradiographs by various optical methods, or by counting the grains.

Aptamers

Aptamers are also useful in the methods of the invention to detect polypeptides such as disease proteins. Aptamers are macromolecules that can recognize targets such as proteins with high specificity and sensitivity.

Nucleic acid aptamers are small molecules isolated from combinatorial libraries by a procedure named systemic evolution of ligands by exponential enrichment (SELEX) (reviewed in Cerchia L et al, FEBS Letters 528 (2002) 12-12). Using this technology aptamers that bind proteins with high target specificity and selectivity can be identified. The affinities can be comparable to antibody antigen interactions. Discrimination between native and denatured protein has been shown (Bianchini et al. Immunol Methods (2001) 252:191-97) making aptamers useful detection agents for the methods of the invention.

Peptide aptamers, also known as paptamers, thioredoxin-insert proteins or pertubagens are artificial proteins where an inserted peptide is expressed on a solvent exposed surface of a structurally stable protein which functions as a scaffold (Crawford M. et al. Brief Funct Genomic Proteomic. 2003 April; 2:72-9). Peptide aptamers can function similarly to antibodies and have dissociation constants that are comparable to, and sometimes better than, antibodies. They can be used to probe immobilized proteins on nitrocellulose (Crawford M. et al. Brief Funct Genomic Proteomic. 2003 April; 2:72-9). Peptide aptamers have been shown to exhibit different affinities for small changes such as single amino acid differences making them useful for the detection of polypeptides that exist in two or more conformations such as disease proteins that exhibit different folding or aggregation conformations.

Accordingly, in one embodiment of the invention, nucleic acid and/or peptide aptamers are used with the methods of the invention to distinguish between wild-type and disease conformation proteins. In one embodiment the disease protein is a prion protein. In another embodiment the disease protein is amyloid-beta. In another embodiment the disease protein is tau protein. In another embodiment the disease protein is alpha-synuclein. In another embodiment the disease protein is SOD-1.

Denaturing and Disaggregation

In the methods, the polypeptide is optionally modified by denaturing the polypeptide, for example with heat, detergent and/or chaotropic agents. The polypeptide is optionally modified by treatment with a disaggregation agent to disaggregate the polypeptide from other polypeptides of the same type, and from other molecules, wherein the disaggregation agent is optionally selected from at least one of the group consisting of chaotropic agents, detergent and heat. Chaotropic agents can include but are not limited to such as guanidine salts, urea, and thiourea.

The inventors have shown that treating proteins with guanidine hydrochloride increases the amount of protected protein detectable.

Combining disaggregation methods can result in optimised disaggregation. For example boiling samples in sodium dodecyl sulfate (SDS; also known as sodium lauryl sulfate) loading buffer can increase solubilization of polypeptides such as disease proteins, increasing the epitopes available for interacting with the detecting agent. For example, boiling samples in SDS loading buffer results in enhanced solubilization, and allows detection of protected epitopes by sandwich ELISA. The sandwich ELISA assay system is able to identify aggregated disease protein in tissue homogenate samples if the samples are boiled in SDS loading buffer after peroxynitrite treatment. At peroxynitrite concentrations greater than 8 mM, there is 2.5-3× as much PrP detected in the acid treated sample as compared to the mock treated sample. Accordingly, in one embodiment the sample is boiled in SDS loading after treatment with modifying agent and before detection with a detecting agent such as an antibody.

Time Resolved Fluorescence (TRF) Two Point ELISA and Dissociation Enhanced Lanthanide FluoroImmunoassay (DELFIA)

As previously mentioned ELISA techniques can be employed by the methods of the invention. Time resolved flouresence two-point ELISA employing Dissociation Enhanced Lanthanide FluoroImmunassay (DELFIA) technology is 1000 fold more sensitive than conventional ELISA techniques and can be used with the methods of the invention to detect polypeptides aggregated in vitro, in neural tissue of transgenic mouse models of neurodegeneration, and in human AD, ALS, PD and LBD patient brain samples.

The DELFIA assay uses a chelated lanthanide-labeled tracer, such as europium (Eu) and time-resolved fluorescence (TRF) to measure output signal (33). The benefit of lanthanide chelates is that their fluorescence is intense and lasts up to 200,000 times longer than conventional fluorophores, allowing signal capture after non-specific interfering fluorescence has faded (particularly critical for biological samples, which may possess considerable intrinsic fluorescence, the emission of which is comparatively short-lived). DELFIA-based systems can measure as little as 100 fmol/well of Eu (33).

In one embodiment of the invention, a chemical modifying agent and antibody are employed in a sensitive capture-detection "sandwich" 96-well plate DELFIA TRF system in the detection of aggregated disease specific proteins described herein, such as Abeta, tau, SOD1, huntingtin alpha-synuclein, islet amyloid polypeptide, resistin and p53.

A two-point EPA increases the specificity for detection of proteins sequestered in aggregates of a clinical sample. In one embodiment, two or more chemically modifiable epitopes are present in each test polypeptide, which would increase the specificity of diagnostic tests employing this technology (e.g., use in two-point ELISA). In one embodiment, the chemically modifiable epitopes are modified by the same chemical. In another embodiment, the epitopes are modified by one of two or more different chemicals. The modified epitopes may be recognized by the same antibody or they may be recognized by two or more different antibodies. For clinical and commercial use, EPA must be sensitive and specific for polypeptides aggregated in vitro and in vivo. With optimal antibodies and chemical modifying regimens, and the DELFIA-TRF system EPA can detect $10^5$-$10^6$ molecules of soluble polypeptides This may correspond to a single polypeptide aggregate, if these aggregates are of similar size to prion protein aggregates in disease (35, 36).

Accordingly in one embodiment, the DELFIA-TRF system EPA can be used to identify disease proteins that are in very low abundance, as low as a single polypeptide aggregate.

Diagnostic and Screening Applications

Effective, efficient and inexpensive diagnostic and screening strategies for antemortem diagnosis of human neurodegenerative diseases are urgently needed, given the aging population and continued financial pressure on the health care system. EPA will achieve clinical utility by detecting polypeptide aggregates in relevant and accessible biological tissues and fluids, for which no present technology exists. In one embodiment the methods of the invention are used to diagnose individuals who have a disease protein related disease. In one embodiment, the invention is used to diagnose individuals who have a neurodegenerative disease. In another embodiment, the invention is used to diagnose individuals who have a neurodegenerative disease selected from the group comprising prion related diseases, AD, HD, ALS and PD. In a further embodiment, the methods of the invention are used post-mortem to determine if the individual had a disease protein related disease.

The methods of the invention are used to detect whether a human has a disease protein related disease. In another embodiment, the methods are used to detect if a non-human animal has a disease protein related disease. In a further embodiment the non-human animal is one of the group comprising cattle, sheep and cervids. In another embodiment, the methods of the invention are used to detect if livestock has a disease protein related disease.

In one embodiment the methods of the invention are used to detect disease proteins in biological specimens. The biological specimens may comprise biological fluids, such as CSF, serum, blood, tears, peritoneal exudates, or urine, or tissue samples such as biopsies or brain tissue. The samples in one embodiment are antemortem samples. In another embodiment they are postmortem samples.

The methods of the invention are useful to quantify detection of soluble form of disease related proteins such as Abeta, tau, SOD1 huntingtin,alpha-synuclein, islet amyloid polypeptide, resistin and p53 protein.

In another embodiment, EPA is used to determine the sensitivity and specificity of aggregate detection in homogenates from CRND8 (human mutant APP) mouse brain and CSF (34) and G93A human mutant SOD1 transgenic mice (13).

In another embodiment the invention is used to determine the sensitivity and specificity of aggregate detection in homogenates from normal (treated and untreated at low pH) and diseased frozen human brain (AD, ALS, PD, LBD).

The methods of the invention are used in one embodiment to ensure preparations derived from mammalian blood or tissues or involving processes where mammalian blood or tissues come into contact with preparations, are free of disease proteins. In one embodiment the preparation is a pharmaceutical product. In another embodiment the preparation is a vaccine. In a further embodiment, the preparation is a cosmetic. In one embodiment, the preparations are tested for prion proteins. In another embodiment, the preparations are tested for amyloid-beta. In another embodiment, the preparations are tested for tau protein. In another embodiment, the preparations are tested for alpha-synuclein. In a further embodiment, the preparations are tested for SOD-1.

In another embodiment, the methods of the invention are used to screen blood, and blood products (eg. blood fractions such as blood plasma or compounds isolated or manufactured from blood) used for transfusions or other medical procedures for disease proteins. In another embodiment, the invention is used to screen organ transplants for disease proteins. In one embodiment, the preparations are screened for prion proteins. In another embodiment, the preparations are screened for amyloid-beta. In one embodiment, the preparations are screened for tau protein. In another one embodiment, the preparations are screened for alpha-synuclein. In a further embodiment, the preparations are screened for SOD-1.

The invention is also useful for ensuring that food sources are free of disease proteins. In another embodiment the methods of the invention are used to test edible products derived from mammals such as meats and meat products; and dairy products. Foods potentially contaminated with neural tissue (such as "mechanically separated meat," and meat cuts containing dorsal root ganglia or other neural tissue) are particularly important to screen for prion contamination.

Instruments that are used for invasive procedures may also be a source of transmitting disease. In one embodiment instruments used for medical and surgical procedures are tested for the presence of disease proteins using methods of the invention. In another embodiment instruments used for dental hygiene are tested for the presence of disease proteins.

In a further embodiment, the invention provides methods to ensure that decontamination methods for removing disease proteins and disease protein containing tissues, have been successful. In one embodiment the methods of the invention are used to assess decontamination procedures in a meat processing plant. In another embodiment the methods of the invention are used to assess decontamination in a food processing plant. In another embodiment instruments used for surgery or dentistry are tested for the presence of disease proteins.

Prognostic Applications

Prion protein conversion, Alzheimer's disease related polypeptide or other disease/disorder polypeptide may be periodically monitored in a subject over time (e.g. at a first time and a second time at least a week or at least a month after the first time) to identify, for example, increased or decreased levels of $PrP^{C}$ or increased or decreased levels of $PrP^{Sc}$ in the subject. The methods of the invention are also useful to measure a subject's level of $PrP^{C}$ or $PrP^{Sc}$ to determine the subject's response to drug therapy. Decreasing levels of prion protein in the subject over time indicate a positive response to drug therapy. The same methods are used with other disease or disorder protein.

Since many neurological diseases are associated with aggregated proteins, similar methods are useful for these diseases and their aggregated proteins, including, but not limited to: amyotrophic lateral sclerosis (superoxide dismutase 1), Alzheimer's disease (amyloid beta), Parkinson's disease (alpha synuclein), Huntington's disease (huntingtin), cancer (p53), diabetes (eg. islet amyloid polypeptide and resistin) and other diseases involving abnormal protein folding, aggregation or post-translational modification. Such a test is useful in the spinal fluid and other bodily fluids in addition to peripheral blood. In Alzheimer's disease, the aggregation status of the amyloid beta peptide is optionally monitored by determining the accessibility of two epitopes detected by the monoclonal antibodies 6E10 and 4G8, in addition to other amyloid beta epitopes, using the methods described in this application, for example, with an anti-6E10 or anti-4G8 antibody (detection agent) known in the art.

Identifying Prion Conversion Inhibitors

Since the invention is useful for detecting differences between polypeptides, the invention further includes an assay for evaluating whether a candidate compound is capable of inhibiting or stabilizing prion conversion or formation of other disease or disorder polypeptides, such as amyloid beta, tau and APP in Alzheimer's disease, SOD1 in amyotrophic lateral sclerosis, alpha-synuclein in Parkinson's and Lewy body disease, huntingtin in Huntington's disease islet amyloid polypeptide and resistin in diabetes and p53 in cancer. The invention also includes compounds for inhibiting or stabilizing prion conversion (or conversion of other disease or disorder polypeptides) identified by the methods described in the application. Decreased protein conversion to an intermediate prion protein substrate or $PrP^{Sc}$ (or other disease or disorder polypeptides shows that the candidate compound is useful for treating prion disease.

The assays of the invention are useful to screen candidate compounds to determine if they inhibit $PrP^{Sc}$ formation (or formation of other disease or disorder polypeptides from wild type protein). Protein may be contacted with a candidate compound in vivo or in vitro and then used in the methods of the invention to determine if wild type protein has been converted to $PrP^{Sc}$ or if $PrP^{Sc}$ has been converted to wild type protein. Similar methods are used with respect to other disease or disorder polypeptides. Recombinant proteins are useful for identifying aggregation inhibitors.

Therefore, the invention also provides methods for identifying substances that inhibit conversion to $PrP^{Sc}$ (e.g. prion protein conversion from wild type protein or intermediate to $PrP^{Sc}$) comprising the steps of:

reacting a polypeptide and a candidate substance, and determining whether the protein has been converted to $PrP^{Sc}$ using the methods of the invention.

Similar methods are optionally performed to identify compounds which stabilize the wild-type prion state, or bind to $PrP^{Sc}$ and block conversion of recruitable PrP isoforms.

The invention also provides methods for identifying substances that inhibit conversion to disease or disorder polypeptides (e.g. conversion from wild type protein to the amyloid beta, tau or APP protein in Alzheimer's disease and other proteins and diseases described in this application) comprising the steps of:

reacting a polypeptide and a candidate substance, and determining whether the protein has been converted to the amyloid beta or APP protein in Alzheimer's disease using the methods of the invention.

Another aspect of the invention provides a method of identifying substances which reverse $PrP^{Sc}$ formation comprising the steps of:

reacting a polypeptide and a candidate substance, and determining whether the $PrP^{Sc}$ has been converted to wild type protein using the methods of the invention.

Another aspect of the invention provides a method of identifying substances which reverse amyloid beta or APP protein in Alzheimer's disease formation comprising the steps of:

reacting a polypeptide and a candidate substance; and determining whether the amyloid beta or APP protein in Alzheimer's disease has been converted to wild type protein using the methods of the invention.

The same methods are used with other polypeptides associated with diseases and disorders described in this application.

Biological samples and commercially available libraries may be tested for substances such as proteins or small organic molecules that bind to a protein. Inhibitors are preferably directed towards specific domains of disease proteins such as prion protein. To achieve specificity, inhibitors should target the unique sequences and or conformational features of the disease protein.

Protein Conformation Detection

The invention includes a method of detecting whether a candidate polypeptide including a target epitope is a non-wild type conformation polypeptide or a wild type conformation polypeptide, comprising:

- contacting the candidate polypeptide with a blocking agent; and
- determining whether the target epitope is inaccessible or accessible to chemical modification by the blocking agent.

The accessibility or inaccessibility of the target epitope is indicative of whether the candidate polypeptide is non-wild type conformation polypeptide or a wild type conformation polypeptide because in one of the non-wild type protein and the wild type protein, the target epitope is accessible. In the other polypeptide, the target epitope is inaccessible.

In one embodiment, the invention includes a method of detecting whether a candidate polypeptide including a target epitope is in a wildtype conformation or a non-wildtype conformation, comprising:

- contacting the polypeptide with a blocking agent that selectively blocks accessible target epitope, wherein in one of the non-wildtype conformation or the wildtype conformation, the target epitope is accessible and reacts with the blocking agent, and wherein in the other conformation, the target epitope is inaccessible and does not react with the blocking agent;
- removing unreacted blocking agent from contact with the polypeptide (eg. by allowing blocking agent to be consumed or degraded in the sample comprising the candidate polypeptide or by physical or chemical removal processes);
- modifying the candidate polypeptide to convert any inaccessible target epitope to accessible target epitope; and
- contacting the polypeptide with a detection agent that binds selectively to target epitope that was converted from inaccessible target epitope to accessible target epitope, wherein binding between detection agent and converted target epitope indicates that prior to conversion the candidate polypeptide was in a conformation in which the target epitope was inaccessible and wherein lack of binding between the detection agent and the target epitope indicates that the polypeptide was in a conformation in which the target epitope was inaccessible, thereby indicating whether the polypeptide was in a wildtype conformation or a non-wildtype conformation.

A polypeptide may have more than two conformations. For example a polypeptide may exist in a wild-type conformation, in a benign misfolded, aggregated or otherwise non-wildtype conformation not associated with disease, and a disease associated conformation (i.e. aggregated in higher order structures). The methods of the invention can be applied to distinguish each of these states through the use of one or more chemical modifying agents and/or one or more detecting agents such as antibodies.

Detection of Intrinsically Modified Polypeptides

The invention also provides a method of detecting polypeptides that exist in two or more conformations wherein the target epitopes in one of the conformations is modified by an intrinsic mechanism. The intrinsic mechanism can include intracellular and/or post-translational modification of a polypeptide such as phosphorylation and/or glycosylation or a modification resulting from an additive used in a process. The intrinsic modification blocks a target epitope obscuring it from detection with a detection agent. The sample of polypeptide is reacted with a blocking agent that reacts with available target epitope in polypeptide that is not intrinsically modified. The intrinsic modification is then removed. For example if the intrinsic modification is phosphorylation, the polypeptide is treated with a phosphatase which removes the phosphorylation and converts the inaccessible target epitope in the previously intrinsically modified polypeptide, to accessible epitope. The polypeptide is then detected with a detecting agent such as an antibody.

Accordingly in one embodiment, the invention provides a method of detecting intrinsically modified target epitopes in a polypeptide having two or more conformations comprising;

- contacting the polypeptide with a blocking agent that selectively blocks accessible target epitope, wherein in one of the non-wildtype conformation or the wildtype conformation, the target epitope is accessible and reacts with the blocking agent, and wherein in the other conformation, the target epitope is inaccessible and does not react with the blocking agent;
- reacting the sample with an agent that removes the intrinsic modification from the intrinsically modified polypeptide target epitope;
- disaggregating and/or denaturing the polypeptide in the sample; and
- probing with a detection agent, such as antibodies against the target epitope, to determine whether the candidate polypeptide is an intrinsically modified polypeptide.

In one application, the methods of the invention can be used to detect whether polypeptides present in food items have been chemically modified by manufacturing processes. For example dairy products can be tested for the presence of formaldehyde, which is used as a bacteriostatic agent. Formaldehyde formylates gamma(2) casein (Pizzano R. et al J. Agric Food Chem (2004) 52:649-54) obscuring modified epitopes from subsequent detection by the detecting agent.

Kits

The methods described herein are optionally performed by utilizing pre-packaged diagnostic kits comprising the necessary reagents to perform any of the methods of the invention. For example, the kits typically include at least one specific nucleic acid, peptide or antibody described herein, which are conveniently used, e.g., in clinical settings, to screen and diagnose patients and to screen and identify those individuals expressing a disease conformation protein. Kit antibodies can comprise whole antibody, antibody fragments, single chain antibody, monoclonal antibody and/or polyclonal antibody. The kits optionally also include at least one chemical agent for modifying epitopes recognized by an antibody or aptamer. The kit is optionally based on ELISA technology such as sandwich ELISA and DELFIA and may employ detergents, precipitation agents (such as phosphotungstic acid) and adsorbents typically used in ELISA technology and known to one skilled in the art. The kit will also include detailed instructions for carrying out the methods of the invention. Recombinant protein are useful for standards in kits.

All such assays could be adapted and optimised to a simple high-throughput platform.

The following non-limiting examples are illustrative of the present invention.

EXAMPLES

Example 1

Figure 1:
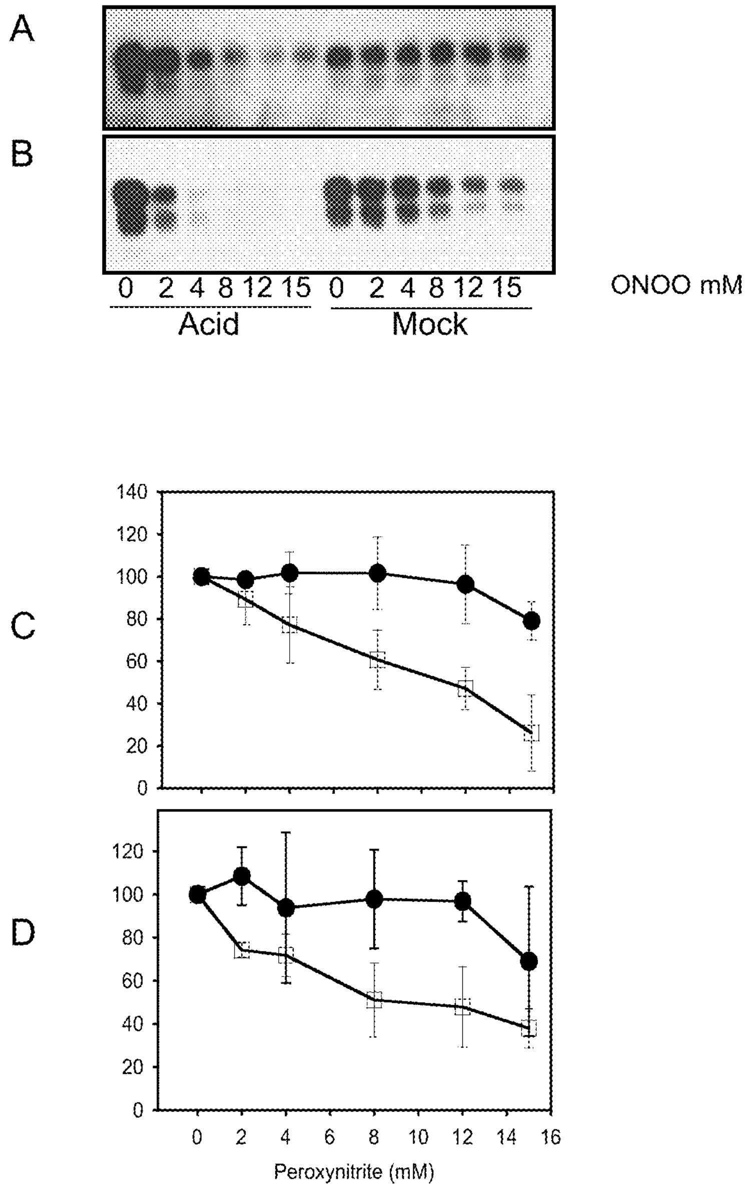
FIG. 1. Brain PRP Aggregated In Vitro by Acid Treatment is Protected from Modification by Peroxynitrite Mock or acid treated human brain homogenate was treated with increasing concentrations of peroxynitrite (ONOO) and then subjected to immunoblotting with 3F4 (panel A) or 6H4 (panel B). Effect of peroxynitrite on the 3F4 (C) and 6H4 (D) epitope in mock (□) and acid treated (●) brain homogenate. Immunoblot films were scanned and band intensities determined by Unscanit software. The results are the combined relative intensities of 3 separate experiments.

Peroxynitrite Reacts Differently with PrP in Normal and Acid Treated or Scrapie Brain Homogenate When brain homogenate is incubated at pH 3.5 in the presence of guanidine, PrP becomes detergent insoluble and is more susceptible to misfolding to a PK-resistant isoform in the presence of $PrP^{Sc}$ (29). This acid treated PrP is a 'model prion' which is partially misfolded and/or aggregated resembling characteristics of $PrP^{Sc}$. When mock (□) and acid treated (●) brain homogenate is incubated with increasing concentrations of peroxynitrite and then subjected to immunoblotting, there is less PrP recognized by both 3F4 (FIGS. 1A and C) and 6H4 (FIGS. 1B and D) in mock treated brain homogenate than in acid treated brain homogenate. The PrP in the acid treated brain homogenate is protected from modification by peroxynitrite.

Example 2

Figure 2:
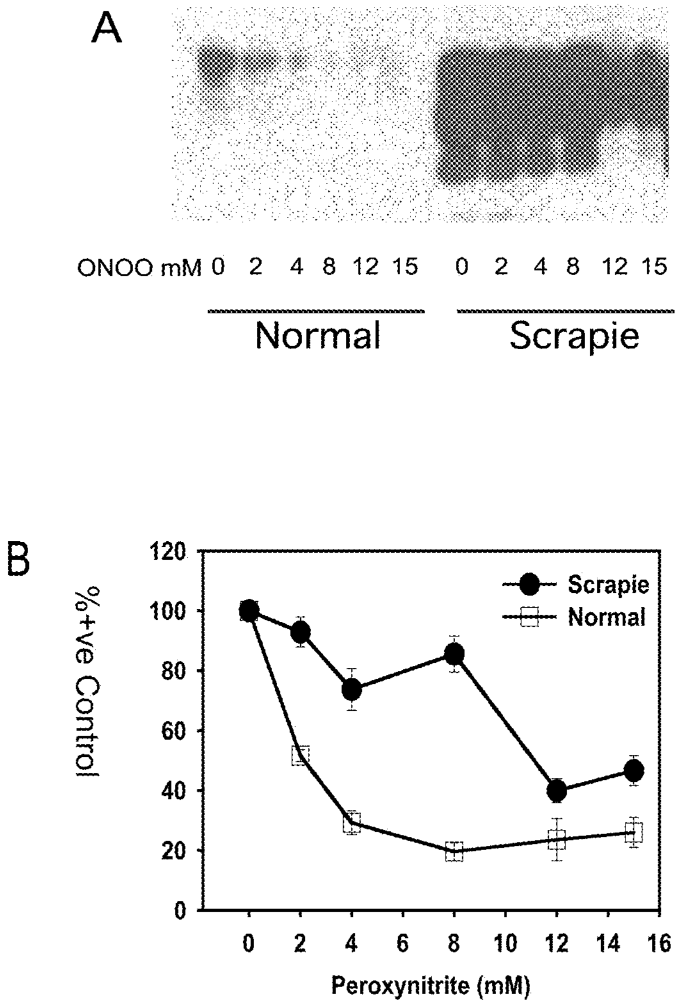
FIG. 2. PrP in Scrapie Infected Hamster Brain is Protected from Modification by Peroxynitrite (A) Effect of peroxynitrite treatment on the 6H4 epitope in scrapie infected hamster brain. (B) The blot in (A) was scanned and relative band intensities determined using Unscanit software. (●) Scrapie infected hamster brain. (□) Normal hamster brain.

PrP in Scrapie Infected Hamster Brain is Protected from Modification by Peroxynitrite The epitope protection phenomenon for 'model prions' as observed in example 1 was also observed for authentic disease-misfolded prion protein in scrapie infected hamster (Ha) brain (FIGS. 2A and B). As with model prions, the 3F4 and 6H4 epitopes of PrP in $Ha^{Sc}$ brain homogenate are protected from modification by peroxynitrite. It is clear that 'model prions' and $HaPrp^{sc}$ share characteristics that provide protection from chemical modification by peroxynitrite, such as differential misfolding or aggregation.

Example 3

Figure 3:
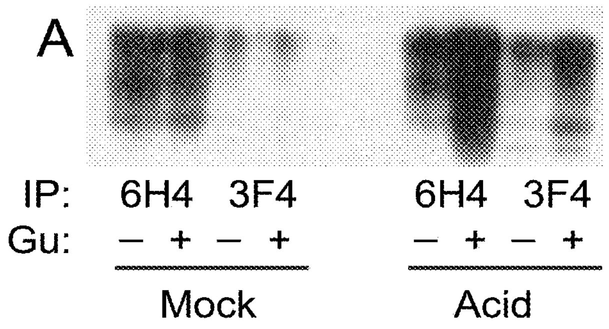
FIG. 3 Protection from Peroxynitrite Induced Modification is Due to Aggregation in Acid Treated Brain (A) Effect of peroxynitrite on the immunoprecipitation (IP) of PrP in mock and acid treated brain homogenate. Brain homogenate was treated with 10 mM peroxynitrite followed by incubation for 2 h at RT with (+) or without (−) 2.5 M guanidine hydrochloride (Gu). The resulting samples were immunoprecipitated with 6H4 or 3F4. More PrP is precipitated in the acid treated sample following treatment with peroxynitrite+Gu whereas in the mock sample, Gu has no effect. This suggests that Gu is able to break up aggregated PrP in the acid sample that is protected from destruction by peroxynitrite. (B) Effect of peroxynitrite on PrP in mock and acid treated brain homogenate as measured by ELISA. Brain homogenate was treated with increasing concentrations of peroxynitrite followed by 2.5 M Gu. Following a 10-fold dilution, the samples were analyzed by sandwich ELISA with 6H4 as the capture Ab and 3F4 as the detection Ab. Similar to the immunoblot and IP data, the results show that misfolded PrP is protected from destruction by peroxynitrite treatment, due to aggregation.
Figure 3:
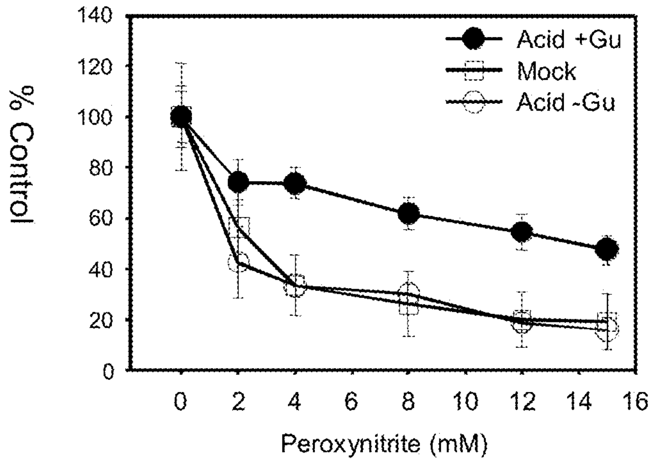

Aggregation is Responsible for the Reduction in Peroxynitrite-Induced Epitope Modification of Misfolded PrP To show that epitope protection of acid treated and scrapie brain was due to aggregation, samples were treated with peroxynitrite and then incubated with or without guanidine before immunoprecipitation. Treatment of the samples with guanidine dissociates aggregates of PrP (43-45) that protect the polypeptide from modification by peroxynitrite. Incubation of mock treated brain with 2.5 M guanidine after peroxynitrite treatment did not show an increase in 3F4 and 6H4 epitopes as revealed by immunoprecipitation (FIG. 3A lanes 1-4). However, when peroxynitrite-treated acid brain homogenate was incubated with guanidine, there was an increase in PrP that could be detected by immunoprecipitation with 3F4 and 6H4 immunobeads (FIG. 3A lanes 5-8). This shows that guanidine is able to dissociate aggregates of acid treated brain homogenate and release PrP that is protected from modification by peroxynitrite. Other means of solubilizing PrP aggregates were used and boiling samples in SDS loading buffer resulted in the greatest observed solubilization to date.

Example 4

Optimization of EPA Parameters

Titration experiments with peroxynitrite, hydrogen peroxide and methylene (based on UV light photolysis of the precursor diazirine) or other modifying agents, identify the optimal conditions for epitope protection in:

1. Normal hamster and human brain "model prions", using immunoblotting and conventional fluorescence ELISA.
2. Infectious prions from hamster and human brain, using immunoblotting analysis and time-resolved fluorescence In each case, brain homogenates are prepared and mixed with increasing concentrations of the modifying agent and processed as described (immunoblotting, and time resolved fluorescence). This defines the type and concentration of chemical agent allowing the maximal distinction between monomeric and aggregated prion proteins. Additional informative control experiments include using recombinant hamster $PrP^{C}$ in buffer and in $PrP^{-/-}$ knockout mouse brain, and by mouse normal and scrapie-infected brain (murine PrP is 6H4+ and 3F4−).

In some cases, infectious prions may have different properties for chemical modification than do "model prions," and brain prions may display different chemical modification properties than do endogenous prions circulating in blood, or $PrP^{Sc}$ detectable in urine of infected animals. One of skill in the art shall readily identify the optimal conditions for authentic endogenous prions using known techniques.

Example 5

EPA Adapted to a Fluorescent ELISA System

The epitope protection assay for aggregated PrP was adapted to a fluorescent sandwich ELISA system using 6H4 as the capture antibody and 3F4 as the detection antibody (FIG. 3B). The sandwich ELISA assay system is able to identify aggregated PrP in acid treated brain homogenate but only if the samples are boiled in SDS loading buffer after peroxynitrite treatment. At peroxynitrite concentrations greater than 8 mM, there is 2.5-3× as much PrP detected in the acid treated sample as compared to the mock treated sample.

Example 6

Detection of a Single Brain Prion

A single brain prion has been estimated to comprise $10^5$-$10^6$ molecules of $PrP^{Sc}$. Detection of $10^8$-$10^9$ molecules of recombinant PrP using conventional fluorescence ELISA has been accomplished. The assay used is about 1000-fold more sensitive for single-prion detection—the necessary sensitivity is provided by the Dissociation enhanced lanthanide fluoroimmunoassay (DELFIA). DELFIA uses a chelated lanthanide-labeled tracer, such as europium (Eu) and time-resolved fluorescence (TRF) to measure output signal. The benefit of lanthanide chelates is that their fluorescence duration is 200,000 times longer than conventional fluorophors, allowing signal capture after non-specific interfering fluorescence has faded (particularly critical for biological samples, which may possess considerable non-specific fluorescence). DELFIA-based systems can measure as little as 100 fmol/well of Eu which is >1000 times more sensitive than conventional ELISA assays, which detects single prions by EPA. The optimal TRF 96-well plate reader for the DELFIA system is manufactured by Wallac-Victor (Perkin-Elmer), and is used to automate sample analysis.

Using an optimal chemical modifier and optimal conditions a sensitive capture 96-well plate assay for detection of hamster and human prions, using the DELFIA TRF system is provided. This is used to:

1. Characterize, optimize and quantify detection of recombinant prion protein by TRF.
2. Determine the sensitivity of the DELFIA-TRF for hamster and human brain prions.

Example 7

Detection of Prion Proteins in Biological Fluids

The EPA achieves commercial utility by detecting $PrP^{Sc}$ in biological tissues and fluids for which no present technology exists. Blood prions are in very low abundance (10-100 prions/mL by bioassay, and protease-resistant PrP in urine is only intermittently/sporadically detectable by precipitation of large fluid volumes. Also, any prospective blood test must contend with high concentrations of $PrP^{C}$ ($10^6$-fold more than $PrP^{Sc}$) and "blocking" by heterologous plasma proteins. Using the optimized chemical modification regimen and the DELFIA-TRF system, the sensitivity thresholds for EPA in blood and urine are determined using:

1. Hamster and human plasma and urine "spiked" with a titration of 263K hamster prions;
2. Plasma and urine from Syrian hamsters "endogenously" infected with 263K prion disease Biological fluids clinically accessible by non-invasive routes provide a substrate for a practical antemortem test for diagnosis and screening of prion infection in humans and animals. The methods of this invention may also be used in post-mortem testing. One of skill in the art readily determines whether EPA with "prion spike" titration in normal blood and urine reveals similar DELFIA-TRF signals to the same prion titration in buffer, showing that the EPA is not affected by "blocking factors" in these biological fluids. Interestingly, preferential "blocking" of $PrP^{Sc}$ by heterologous proteins may actually enhance epitope protection to chemical modifying agents. If decreased detection of prions in blood or urine is observed, pre-clearing strategies are readily employed to enhance $PrP^{Sc}$ detection with detergents, precipitating agents, and adsorbents typically used in commercial ELISA assays which are known to one skilled in the art.

Human and bovine plasma and urine and other bodily fluids are tested using optimized EPA conditions and compared to samples from human variant CJD and BSE, respectively. Although the monoclonal antibody 6H4 recognizes PrP from all relevant species, other antibodies (commercially available) are used for the DELFIA TRF system for cattle, sheep, and cervids, which lack the 3F4 epitope. Other antibodies and epitopes useful in methods described in this application will be readily apparent to those of skill in the art.

Example 8

Detection of Aggregated Amyloid Beta (Abeta) Using EPA

Figure 4:
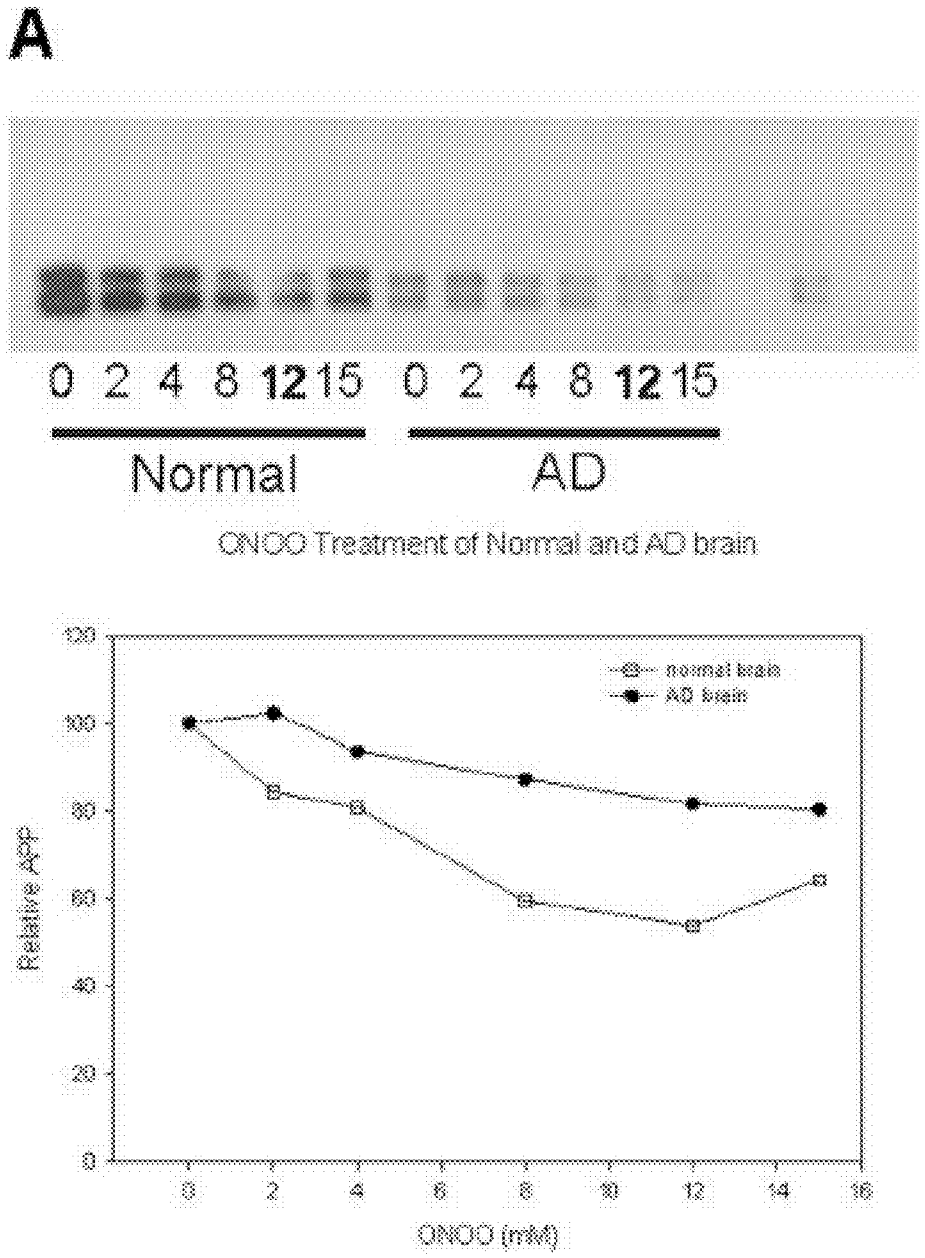
FIG. 4 Detection of Aggregated Amyloid Beta (Abeta)) Using EPA

Amyloid beta peptide (Abeta) is a normal cleavage product of the proteolytic processing of amyloid precursor protein (APP). Abeta accumulates in discrete plaques in affected regions of Alzheimer's disease brain, and triggers neuronal death and gliosis observed in this disease. Plaque Abeta is aggregated and rich in beta-sheet structure, in contrast to the Abeta region of APP expressed by normal cells. Using epitope protection technology, it was demonstrated that the 6E10 epitope in the Abeta region of APP is less accessible to peroxynitrite modification in Alzheimer's disease brain compared to normal brain (FIG. 4 panel A). Similarly, the 6E10 epitope is partially protected in brain homogenates that have been treated at low pH to induce protein aggregation (FIG. 4 panel B). Abeta 1-42 peptide aggregated by overnight incubation at 1 mg/ml in water shows prominent epitope protection of the 6E10 epitope to peroxynitrite modification, in comparison with soluble non-aggregated Abeta 1-42 (FIG. 4 panel C). A further example of this phenomenon is presented in FIG. 4, panel D which shows normal (○) and aggregated (●) Abeta 1-42 treated with increasing concentrations of peroxynitrite, subjected to immunoblotting with 6E10 antibody.

The 6E10 epitope of APP is also unavailable to peroxynitrite modification in AD brain homogenates and in normal brain homogenates aggregated by low pH, but normal untreated brain does not show this protection (FIG. 4 panel A and B), showing molecular interaction in vivo of APP with an Abeta-domain blocking molecule (perhaps Abeta itself; ref. 9).

The sensitive and specific EPA detection of aggregated Abeta in biological fluids (such as blood and spinal fluid), or protection of Abeta epitopes in APP in cells and tissues, provides an antemortem diagnostic test for Alzheimer's disease. The methods of the invention described in this application are used for this diagnostic test.

Detection of Aggregated Tau Protein by EPA

Dying neurons release intracellular proteins such as tau into the CSF (39) and likely ultimately blood. Tau studies are directly performed on brain specimens including Alzheimer patient samples and control brain.

Example 9

Detection of Aggregated Superoxide Dismutase 1 (SOD1) by EPA

SOD1-containing cytoplasmic inclusions are detected in many diseased motor neurons from familial and sporadic ALS patients (15), and in most transgenic mouse (16, 17) and tissue culture models (18) of the disease. Human SOD1 can be aggregated in vitro. Further SOD1 is modifiable by succinic anhydride and DEPC. This property can be exploited by EPA technology to discriminate between aggregated and unaggregated SOD1 protein.

Purified SOD1 from human erythrocytes (Sigma) was aggregated in a metal-catalyzed oxidation reaction. Soluble SOD1 was treated with varying concentrations of DEPC, denatured with heat, and immunoblotted with anti-SOD1 antibodies. Western blotting shows that increasing concentrations of DEPC are associated with decreases in antibody binding in soluble SOD1 (FIG. 5) showing that sites are available for modification by a blocking agent.

Antibodies against SOD1 selected a priori for utility in EPA are used to distinguish disease specific aggregated SOD1 from wildtype SOD1. Relevant factors include:

1) selecting an epitope on the molecular surface of the native dimer to be accessible to chemical modification in the native soluble state;
2) identifying a linear epitope to optimize detection in the denatured state on immunoblots and ELISA;
3) immunogenicity;
4) uniqueness to SOD1; and
5) presence of acidic amino acids (Glu and Asp) that are readily modified by epoxides.

The five SOD1 sequences that meet these criteria are: 22QKESNG27 (SEQ ID NO:4); 51EDNTAGCTSA60 (SEQ ID NO:5); 74PKDEERHV81 (SEQ ID NO:6); 89ADKDG93 (SEQ ID NO:7); and 127GKGGNEQSTK136 (SEQ ID NO:8) (in bold: solvated side chains).

Additionally the electrostatic loop sequence and zinc binding loop of human SOD1 are surface-accessible sequences and are involved in aggregate formation (Elan, J. et al. Nature Structural Biology (2003) 10:461-67).

These sequences are:

```
Electrostatic loop of human SOD1:
                                (SEQ ID NO: 9)
Asp Leu Gly Lys Gly Gly Asn Glu Glu Ser

Thr Lys Thr Gly Asn Ala Gly Ser

Zinc-binding loop of human SOD1:
                                (SEQ ID NO: 10)
Asn Pro Leu Ser Arg Lys His Gly Gly Pro

Lys Asp Glu Glu
```

Example 10

Detection of Aggregated Alpha-Synuclein by EPA

Most cases of Parkinson's disease are sporadic, but both sporadic and familial forms of the disease are characterized by intracellular Lewy bodies in dying neurons of the substantia nigra, a population of midbrain neurons (~60,000) that are selectively decimated in PD. Lewy bodies are predominantly composed of alpha-synuclein (22). Mutations in the gene encoding alpha-synuclein have been found in patients with familial Parkinson's disease (reviewed in 23). Another gene associated with autosomal recessive PD is parkin, which is involved in alpha-synuclein degradation (22, 23). Diffuse cortical Lewy bodies composed of alpha-synuclein are observed in Lewy body disease (LBD), a dementing syndrome associated with Parkinsonian tone changes, hallucinations, and rapid symptom fluctuation (24).

The Syn-1 epitope is optionally blocked by chemical modification of recombinant alpha-synuclein with DEPC (histidine reactive), and alpha-synuclein aggregated in vitro is partially protected from DEPC epitope blocking (FIG. 6).

Aggregated alpha-synuclein in vitro is protected from modification by DEPC whereas normal protein is not. Three mg/mL mutant A53T alpha-synuclein was incubated at 37° C. for three days for aggregation. The aggregation reaction was applied to ultracentrifugation. Normal protein prior to aggregation (containing soluble alpha-synuclein) and the pellet resuspension from the ultracentrifugation (containing insoluble alpha-synuclein) were treated with varying concentrations of DEPC, denatured with heat, and blotted with Syn-1 antibody from BD Biosciences. FIG. 6A shows that increasing concentrations of DEPC are associated with a gradual decrease in antibody binding in normal alpha-synuclein. Insoluble alpha-synuclein shows little change in antibody binding with increasing concentrations of DEPC until the DEPC concentrations reach 1 mM. A graphical representation of these findings is presented in FIG. 6B. The extent of antibody binding to DEPC-treated normal alpha-synuclein (■) decreases gradually overall but more rapidly at higher concentrations of DEPC. Insoluble alpha-synuclein (▲), on the other hand, shows little change in the extent of antibody binding. The last data point at 0.01 M DEPC for insoluble alpha-synuclein increases due to the darkening of the film.

Example 11

Detection of Aggregated Proteins in CSF

Extracellularly deposited Abeta has been quantified in CSF and blood of patients with AD and normal controls (6-8). Intracellular neuronal proteins, such as alpha-synuclein, have been detected in CSF and blood (37, 38). Dying neurons release intracellular proteins 14-3-3, neuron-specific enolase, tau, and alpha-synuclein into the CSF (39), and likely ultimately blood. A proportion of released protein in disease is in an aggregated form. EPA technology is applied to determine the proportion of polypeptide aggregates in CSF samples from patients with AD, ALS, PD, and LBD. Signal is measured for polypeptides disaggregated before and after chemical treatment, representing "total" and "protected" epitopes, respectively, to determine the proportion of polypeptide in the aggregated state. Using the optimized mAbs and chemical modification regimens, and the DELFIA-TRF system, EPA sensitivity is determined in:

1. Normal CSF "spiked" with polypeptides aggregated in vitro.
2. CSF from patients with AD, ALS, PD, and LBD.

The proportion of aggregated polypeptides in a CSF sample, is determined even if it constitutes only $10^5$-$10^6$ molecules. Detergents, precipitating agents (such as phosphotungstic acid), and adsorbents typically used in commercial ELISA assays to enrich for relevant species are optionally employed. Biological fluids clinically accessible by non-invasive routes provides an ideal substrate for a practical antemortem test for diagnosis and screening of neurodegenerative diseases.

Materials and Methods

Materials

Recombinant hamster PrP (rhaPrP) and 6H4 was from Prionics. Recombinant human PrP (rhuPrP) was from Roboscreen. Biotin-3F4 and 3F4 were from Signet. 3F4 reacts against MKHM (SEQ ID NO:1) and 6H4 reacts against DYEDRYYRE (SEQ ID NO:2). 6E10 anti-Abeta (from Signet) reacts against EFRHDS (SEQ ID NO:3) (residues 3-8).

Other antibodies and the epitopes recognized if known, are provided in table 1 above.

Preparation of Acid-Misfolded PrP and APP.

Acid misfolded PrP was used as "model prions" in this study and was prepared as in (29). Briefly, 100 μl of 10% brain homogenate was mixed with an equal volume of 3.0 M GdnHCl (final concentration 1.5 M) in PBS at pH 7.4 or pH 3.5 adjusted with 1 N HCl, followed by rotation at room temperature. After 5 h incubation, samples were methanol precipitated with 5 volumes of ice-cold methanol and pellets were resuspended in 100 μl of lysis buffer. The samples treated at pH 7.4 were designated as mock-treated samples.

Peroxynitrite Treatment of Brain Homogenates

An aliquot (18 μl) of normal or misfolded/diseased brain homogenate was vortexed while 2 μl of peroxynitrite in 100 mM NaOH/60 mM $H_2O_2$ was added to give a final peroxynitrite concentration of 0-15 mM. After vortexing for a further 15 s, the samples were subjected to Western blotting, immunoprecipitation or sandwich ELISA.

DEPC Treatment of Erythrocyte SOD1

Purified SOD1 from human erythrocytes (Sigma) is aggregated in a metal-catalyzed oxidation reaction consisting of 40 μM SOD1, 4 mM ascorbic acid, and 0.2 mM $CuCl_2$ in 10 mM Tris-acetate buffer (pH7) at 37° C. for three days. Ultracentrifuged supernatant (containing soluble SOD1) and the pellet resuspension (containing insoluble SOD1) are treated with varying concentrations of DEPC (100 μM to 0.1 M), denatured with heat, and immunoblotted with anti-SOD1.

Western Blotting

Samples were boiled in SDS loading buffer (62 mM Tris (pH 6.8), 10% glycerol, 2% SDS, 5% beta-mercaptoethanol and 0.01% bromphenol blue) for 5 min. and separated on 12% Tris-Glycine polyacrylamide gels followed by transfer to Hybond-P. PrP was detected using 3F4 (1:50000) 6H4 (1:10000) or 6E10 (1:1000) as the primary antibodies and HRP-conjugated goat anti-mouse (1:10000) as the secondary antibody followed by exposure to ECL-Plus and visualization by exposure to Kodak X-OMAT film. Band intensities were quantitated using UnScan-IT software.

Immunoprecipitation

Samples were incubated with 50 μl of Ab-conjugated (100 μg/ml) Dynal M-280 magnetic beads in a final volume of 1 ml binding buffer (3% NP-40; 3% Tween-20) for 3 h at room temperature with rotation. Beads were washed in wash buffer (2% NP-40; 2% Tween-20) ×3 and boiled in 30 μl SDS loading buffer without beta-mercaptoethanol for 5 min. Supernatants were analyzed by Western blotting as described above.

Sandwich ELISA

The capture antibody (6H4; 1:5000 in 50 mM bicarbonate binding buffer, pH 9.6) was bound to an opaque 96-well plate (Nunc Maxisorp) by overnight incubation at 4° C. After blocking with 1% BSA in 0.05% TBST for 2 h, plates were washed 3× in TBST and incubated overnight at 4° C. with standard concentrations of rhuPrP or rHaPrP along with unknown brain homogenates. Plates were washed 3× and incubated with the detecting antibody biotin-3F4 (1:5000) at RT for 1 h. After washing 3×, avidin-HRP (1:5000) was added and incubated for 30 min. at RT. Following a final wash step (×3) the plate was developed with Quantablu fluorescent substrate for 10-90 min at RT and fluorescent intensities determined with an excitation of 325 nm and emission of 420 nm.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications, including U.S. application No. 60/496,381 (entitled Methods of Detecting Prion Protein (Cashman & Lehto), filed on Aug. 20, 2003 and U.S. application No. 60/497,362 (entitled Epitope Protection Assay (Cashman & Lehto), filed on Aug. 21, 2003 and the Corresponding Canadian applications nos. 2,437,675 and 2,437,999 are herein incorporated by reference in their entirety to the same extent as if each individual publication, patent or patent application was specifically and individually indicated to be incorporated by reference in its entirety.

REFERENCES

1. Prusiner S B. Shattuck lecture—neurodegenerative diseases and prions. N Engl J Med. 344:1516-26, 2001.
2. Caselli R J. Current issues in the diagnosis and management of dementia. Semin Neurol. 23:231-40, 2003.
3. Cashman N R. Do the benefits of currently available treatments justify early diagnosis and announcement? Arguments for. Neurology. 53(Suppl 5):550-2, 1999.
4. Selkoe D J. Alzheimer's disease: genes, proteins, and therapy. Physiol Rev. 81:741-66, 2001.
5. Puglielli L, Tanzi R E, Kovacs D M. Alzheimer's disease: the cholesterol connection. Nat Neurosci. 6:345-51, 2003.
6. Mehta P D, Pirttila T, Mehta S P. Plasma and cerebrospinal fluid levels of amyloid beta proteins 1-40 and 1-42 in Alzheimer disease. Arch Neurol. 57:100-5, 2000.
7. Clark C M, Xie S, Chittams J et al. Cerebrospinal fluid tau and beta-amyloid: how well do these biomarkers reflect autopsy-confirmed dementia diagnoses? Arch Neurol. 60:1696-702, 2003.
8. Green A J. Cerebrospinal fluid brain-derived proteins in the diagnosis of Alzheimer's disease and Creutzfeldt-Jakob disease. Neuropathol Appl Neurobiol. 28:427-40, 2002.
9. Lorenzo A, Yuan M, Zhang Z, et al. Amyloid beta interacts with the amyloid precursor protein: a potential toxic mechanism in Alzheimer's disease. Nat Neurosci. 3:460-4, 2000.
10. Rosen D R, Siddique T, Patterson D. et al. Mutations in Cu/Zn superoxide dismutase gene are associated with familial amyotrophic lateral sclerosis. Nature. 362:59-62, 1993.
11. Deng H X, Hentati A, Tainer J A et al. Amyotrophic lateral sclerosis and structural defects in Cu,Zn superoxide dismutase. Science. 20; 261:1047-51, 1993.
12. Anderson, P M in Brown R H, Meininger V, Swash eds. Amyotrophic Lateral Sclerosis. London: Martin Dunitz. 2000.
13. Gurney, M. E., Pu, H., Chiu, A. Y., et al. Motor neuron degeneration in mice that express a human Cu,Zn superoxide dismutase mutation. Science 264:1772-1775, 1994.
14. Ripps, M. E., Huntley, G. W., Hof, P. R., et al. Transgenic mice expressing an altered murine superoxide dismutase gene provide an animal model of amyotrophic lateral sclerosis. Proc. Natl. Acad. Sci. U.S.A 92: 689-693, 1995.
15. Kato, S., Takikawa, M., Nakashima, K., et al. New consensus research on neuropathological aspects of familial amyotrophic lateral sclerosis with superoxide dismutase 1 (SOD1) gene mutations: inclusions containing SOD1 in neurons and astrocytes. Amyotroph. Lateral. Scler. Other Motor Neuron Disord. 1: 163-184, 2000.
16. Bruijn, L. I., Becher, M. W., Lee, M. K. ALS-linked SOD1 mutant G85R mediates damage to astrocytes and promotes rapidly progressive disease with SOD1-containing inclusions. Neuron 18: 327-338, 1997.
17. Bruijn, L. I., Houseweart, M. K., Kato, S., Aggregation and motor neuron toxicity of an ALS-linked SOD1 mutant independent from wild-type SOD1. Science 281: 1851-1854, 1998.
18. Durham, H. D., Roy, J., Dong, L., and Figlewicz, D. A. Aggregation of mutant Cu/Zn superoxide dismutase proteins in a culture model of ALS. J. Neuropathol. Exp. Neurol. 56:523-530, 1997.
19. Li Y K, Chir J, Chen F Y. Catalytic mechanism of a family 3 beta-glucosidase and mutagenesis study on residue Asp-247. Biochem J 355(Pt 3):835-40, 2001
20. Rose R B, Rose J R, Salto R, Craik C S, Stroud R M. Structure of the protease from simian immunodeficiency virus: complex with an irreversible nonpeptide inhibitor. Biochemistry 32:12498-507, 1993.
21. Olanow C W. The scientific basis for the current treatment of Parkinson's disease. Annu Rev Med 55:41-60, 2004.
22. Iwatsubo T. Aggregation of alpha-synuclein in the pathogenesis of Parkinson's disease. J Neurol 250 Suppl 3:III11-4, 2003.
23. Eriksen J L, Dawson T M, Dickson D W, Petrucelli L Caught in the act: alpha-synuclein is the culprit in Parkinson's disease. Neuron 40:453-6, 2003.
24. McKeith I, Mintzer J, Aarsland D et al. Dementia with Lewy bodies. Lancet Neurol 3:19-28, 2004.

25. Alvarez B, Ferrer-Sueta G, Freeman B A, Radi R. Kinetics of peroxynitrite reaction with amino acids and human serum albumin. J Biol Chem 274:842-8, 1999.
26. Alvarez B, Radi R Peroxynitrite reactivity with amino acids and proteins. Amino Acids 25:295-311, 2003.
27. Sokol P P, Holohan P D, Ross C R. Arginyl and histidyl groups are essential for organic anion exchange in renal brush-border membrane vesicles. J Biol Chem 263:7118-23, 1988.
28. Zou W-Q, Yang D-S, Fraser P E, Cashman N R, Chakrabartty A. All-or-none fibrillogenesis of a prion peptide. Europ J Biochem 268:4885-4891, 2001.
29. Zou W-Q, Cashman N R. Acidic pH and detergents enhance in vitro conversion of human brain PrPC to a PrPSc-like form. J Biol Chem 277:43942-43947 2002.
30. Rakhit R, Cunningham P, Furtos-Matei A, Dahan S, Qi X-F, Crow J, Cashman N R, Kondejewski L H, Chakrabartty A. Oxidation-induced misfolding and aggregation of superoxide dismutase and its implications for amyotrophic lateral sclerosis. J Biol Chem 277:47551-62002, 2002.
31. Paramithiotis E, Pinard M, Lawton T, LaBoissiere S, Leathers V L, Zou W-Q, Estey L A., Kondejewski L H, Francoeur G P, Papadopoulos M, Haghighat A, Spatz S J, Tonelli Q, Ledebur H C, Chakrabartty A, Cashman N R. A PrPSc-specific immunological epitope. Nature Medicine 9:893-9, 2003.
32. Rakhit R, Crow J P, Lepock J R, Kondejewski L H, Cashman N R, Chakrabartty A. Monomeric Cu/Zn superoxide dismutase is a common misfolding intermediate in the oxidation models of sporadic and familial ALS. J Biol Chem e-pub January 2004.
33. MacGregor, I., Hope, J., Barnard, G. Application of a time-resolved fluoroimmunoassay for the analysis of normal prion protein in human blood and its components. Vox Sang 77:88-96, 1999.
34. Chishti M A, Yang D S, Janus C et al. Early-onset amyloid deposition and cognitive deficits in transgenic mice expressing a double mutant form of amyloid precursor protein 695. J Biol Chem 276:21562-70, 2001.
35. Bolton D. C., McKinley M. P., and Prusiner S. B. Identification of a protein that purifies with the scrapie prion. Science 218:1309-1311, 1982.
36. Beekes M., Baldauf E., and Diringer H. Sequential appearance and accumulation of pathognomic markers in the central nervous system of hamsters orally infected with scrapie J. Gen. Virol 77:1925-1934, 1996.
37. Borghi R, Marchese R, Negro A, et al. Full length alpha-synuclein is present in cerebrospinal fluid from Parkinson's disease and normal subjects. Neurosci Lett. 287:65-7, 2000.
38. El-Agnaf O M, Salem S A, Paleologou K E, et al. Alpha-synuclein implicated in Parkinson's disease is present in extracellular biological fluids, including human plasma. FASEB J 17:1945-7, 2003.
39. Verbeek M M, De Jong D, Kremer H P. Brain-specific proteins in cerebrospinal fluid for the diagnosis of neurodegenerative diseases. Ann Clin Biochem 40(Pt 1):25-40, 2003.
40. Coulthart, M. B. and Cashman, N. R. (2001) CMAJ. 165, 51-58.
41. Prusiner, S. B. (1998) Proc. Natl. Acad. Sci. U.S.A 95, 13363-13383.
42. Will, R. G., Ironside, J. W., Zeidler, M., Cousens, S. N., Estibeiro, K., Alperovitch, A., Poser, S., Pocchiari, M., Hofman, A., and Smith, P. G. (1996) Lancet 347, 921-925.
43. Kocisko, D. A., Lansbury, P. T., Jr., and Caughey, B. (1996) Biochemistry 35, 13434-13442.
44. Barnard, G., Helmick, B., Madden, S., Gilbourne, C., and Patel, R. (2000) Luminescence. 15, 357-362.
45. Meyer, R. K., Oesch, B., Fatzer, R., Zurbriggen, A., and Vandevelde, M. (1999) J. Virol. 73, 9386-9392.
46. Kang, S. C., Li, R., Wang, C., Pan, T., Liu, T., Rubenstein, R., Barnard, G., Wong, B. S., and Sy, M. S. (2003) J. Pathol. 199, 534-541.
47. Shaked G M, Shaked Y, Kariv-Inbal Z, Halimi M, Avraham I, Gabizon R. (2001) J Biol Chem. 276, 31479-82.
48. Ross C A et al. Nature Medicine, (2004) 510-17.)
49. Davies S W et al Cell 90, 537-548 (1997).
50. Scherzinger E et al. Proc. Natl. Acad. Sci. USA 96, 4604-9, (1999).
51. Sen S et al Protein Sci. (2003) 12:953-962.
52. Llewelyn C A et al. Lancet (2004) 363:417-421.
53. Peden A H et al. Lancet (2004) 364:527-529.
54. Andreoletti O et al. Nat. Med. (2004) 6:591-593.
55. Thomzig A et al. J Clin Invest. (2004) 10:1465-72.
56. Glatzel M et al. N Engl J Med. (2003) 349:1812-20.
57. Bosque P J et al. Proc Natl Acad Sci USA. (2002) 99:3812-7.

We claim:

1. A method of detecting whether a sample contains a beta-amyloid polypeptide (Abeta) in an aggregated conformation, comprising: contacting the polypeptide in the sample with at least 2 mM concentration of peroxynitrite to block an accessible target epitope on the Abeta, wherein in the wildtype conformation, the target epitope is accessible and chemically reacts with the peroxynitrite, and wherein in the aggregated conformation, the target epitope is inaccessible and the target epitope cannot chemically react with the peroxynitrite; and wherein the target epitope is EFRHDS (SEQ ID NO:3) or amino acid residues at positions 18-22 of human Abeta;

removing unreacted peroxynitrite from contact with the Abeta;

disaggregating or denaturing the Abeta to convert any inaccessible target epitope to the accessible target epitope;

contacting the sample with an antibody that binds selectively to the target epitope that was converted from the inaccessible target epitope to the accessible target epitope, the antibody having at least a 2-fold increased specificity for the converted target epitope compared to the target epitope reacted with peroxynitrite; and detecting the presence of binding between the antibody and the converted target epitope, wherein binding between the antibody and the converted target epitope indicates that the Abeta was in an aggregated conformation.

2. The method of claim 1, wherein the polypeptide is denatured by heat and/or detergent and/or chaotropic agents.

3. The method of claim 1, wherein the polypeptide is modified by treatment with a disaggregation agent to disaggregate the polypeptide from the aggregated polypeptides.

4. The method of claim 1, wherein the disaggregation agent is selected from at least one of the group consisting of chaotropic agents, detergent and heat.

5. The method of claim 1, wherein the detergent comprises SDS.

6. The method of claim 1, wherein prior to contacting the peroxynitrite with the Abeta polypeptide, the Abeta polypeptide is in a sample that is pretreated by one or more of the following methods: adsorption, precipitation, or centrifugation.

7. The method of claim 1, wherein prior to contacting the peroxynitrite with the Abeta polypeptide, the target epitope is mapped.

8. The method of claim 1, wherein the polypeptide is in a postmortem or antemortem sample selected from the group of: CSF, serum, blood, urine, biopsy sample or brain tissue.

9. The method of claim 1, wherein the antibody comprises the antibody 6E10 or 4G8 and/or binds specifically to EFRHDS (SEQ ID NO:3) or amino acid residues at positions 18-22 of human Abeta.

* * * * *